US010226563B2

(12) United States Patent
Garrison et al.

(10) Patent No.: US 10,226,563 B2
(45) Date of Patent: Mar. 12, 2019

(54) METHODS AND SYSTEMS FOR TREATMENT OF ACUTE ISCHEMIC STROKE

(75) Inventors: Michi E. Garrison, Half Moon Bay, CA (US); Tony M. Chou, Hillsborough, CA (US); Gregory M. Hyde, Menlo Park, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 0 days.

(21) Appl. No.: 12/645,179

(22) Filed: Dec. 22, 2009

(65) Prior Publication Data
US 2010/0217276 A1   Aug. 26, 2010

Related U.S. Application Data

(60) Provisional application No. 61/140,601, filed on Dec. 23, 2008, provisional application No. 61/176,463, filed on May 7, 2009.

(51) Int. Cl.
*A61M 1/36* (2006.01)
*A61B 17/3207* (2006.01)
(Continued)

(52) U.S. Cl.
CPC ... *A61M 1/3621* (2013.01); *A61B 17/320725* (2013.01); *A61M 1/3613* (2014.02);
(Continued)

(58) Field of Classification Search
CPC .. A61M 1/3613; A61M 1/3655; A61M 5/165;
A61M 2005/1657; A61M 1/3621; A61M 25/0662; A61M 2025/0681; A61M 2025/0687; A61M 25/10; A61M 2025/1052; A61M 29/00; A61M 1/3653; A61M 2025/0031; A61M 2025/0042;
(Continued)

(56) References Cited

U.S. PATENT DOCUMENTS 4,771,777 A   9/1988   Horzewski
4,840,690 A   6/1989   Melinyshyn
(Continued)

FOREIGN PATENT DOCUMENTS

DE   102006039236   2/2008
EP      0427429 A2   5/1991
(Continued)

OTHER PUBLICATIONS

Adami, M.D., et al., (2002) "Use of the Parodi Anti-Embolism System in Carotid Stenting: Italian Trial Results" J Endovasc Ther 9:147-154.
(Continued)

*Primary Examiner* — Jocelin Tanner
(74) *Attorney, Agent, or Firm* — Mintz Levin Cohn Ferris Glovsky and Popeo, P.C.

(57) ABSTRACT

Methods and devices are disclosed that enable safe, rapid and relatively short and straight access to the cerebral arteries for the introduction of interventional devices to treat acute ischemic stroke. In addition, the disclosed methods and devices provide means to securely close the access site to the cerebral arteries to avoid the potentially devastating consequences of a transcervical hematoma.

11 Claims, 26 Drawing Sheets

(51) Int. Cl.
*A61M 25/06* (2006.01)
*A61M 25/10* (2013.01)
*A61N 7/00* (2006.01)
*A61B 17/22* (2006.01)
*A61F 2/01* (2006.01)
*A61M 25/00* (2006.01)
*A61M 29/02* (2006.01)

(52) U.S. Cl.
CPC ........ *A61M 1/3656* (2014.02); *A61M 1/3659* (2014.02); *A61M 25/0662* (2013.01); *A61M 25/10* (2013.01); *A61N 7/00* (2013.01); *A61B 17/22004* (2013.01); *A61B 2017/320716* (2013.01); *A61B 2017/320733* (2013.01); *A61F 2/013* (2013.01); *A61M 1/3653* (2013.01); *A61M 25/007* (2013.01); *A61M 29/02* (2013.01); *A61M 2025/0031* (2013.01); *A61M 2025/0037* (2013.01); *A61M 2025/0042* (2013.01); *A61M 2025/0681* (2013.01); *A61M 2025/1052* (2013.01); *A61M 2205/7545* (2013.01); *A61N 2007/0043* (2013.01)

(58) Field of Classification Search
CPC ........... A61B 17/320725; A61B 2017/320733; A61B 2017/320716; A61F 2/013; A61F 2002/015; A61F 2002/016; A61F 2002/018; A61F 2/04; A61F 2/06
USPC ....... 606/159, 127, 128, 213, 194, 190–192, 606/200; 604/22, 8, 9, 131, 103.01, 6.12, 604/187, 509, 500, 151, 30–36, 43, 604/167.01–167.06, 245–249, 96.01
See application file for complete search history.

(56) References Cited

U.S. PATENT DOCUMENTS

| | | |
|---|---|---|
| 4,865,581 A | 9/1989 | Lundquist |
| 4,921,478 A * | 5/1990 | Solano et al. ................ 604/509 |
| 4,921,479 A | 5/1990 | Grayzel |
| 4,946,440 A | 8/1990 | Hall |
| 5,135,484 A | 8/1992 | Wright |
| 5,250,060 A | 10/1993 | Cabo |
| 5,312,356 A | 5/1994 | Engelson et al. |
| RE34,633 E | 6/1994 | Sos et al. |
| 5,324,262 A | 6/1994 | Fischell et al. |
| 5,328,471 A | 7/1994 | Slepian |
| 5,380,284 A | 1/1995 | Don Michael |
| 5,429,605 A | 7/1995 | Richling |
| 5,437,632 A | 8/1995 | Engelson |
| 5,443,454 A | 8/1995 | Tanabe et al. |
| 5,454,795 A | 10/1995 | Samson |
| 5,456,667 A | 10/1995 | Ham |
| 5,476,450 A | 10/1995 | Ruggio |
| 5,484,412 A | 1/1996 | Pierpont |
| 5,484,418 A | 1/1996 | Quiachon et al. |
| 5,492,530 A | 2/1996 | Fischell et al. |
| 5,496,294 A | 3/1996 | Hergenrother et al. |
| 5,522,836 A | 6/1996 | Palermo |
| 5,542,937 A | 8/1996 | Chee et al. |
| 5,558,635 A | 9/1996 | Cannon |
| 5,573,520 A | 11/1996 | Schwartz et al. |
| 5,599,326 A | 2/1997 | Carter |
| 5,628,754 A | 5/1997 | Shevlin et al. |
| 5,658,264 A | 8/1997 | Samson |
| 5,667,499 A | 9/1997 | Welch et al. |
| 5,695,483 A | 12/1997 | Samson |
| 5,702,373 A | 12/1997 | Samson |
| 5,707,376 A | 1/1998 | Kavteladze et al. |
| 5,730,734 A | 3/1998 | Adams et al. |
| 5,749,849 A | 5/1998 | Engelson |
| 5,749,858 A | 5/1998 | Cramer |
| 5,794,629 A | 8/1998 | Frazee |
| 5,795,341 A | 8/1998 | Samson |
| 5,810,869 A | 9/1998 | Kaplan et al. |
| 5,827,229 A | 10/1998 | Auth et al. |
| 5,833,650 A | 11/1998 | Imran |
| 5,836,926 A | 11/1998 | Peterson et al. |
| 5,836,955 A * | 11/1998 | Buelna ................ A61B 17/04 606/144 |
| 5,846,251 A | 12/1998 | Hart |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,334 A | 3/1999 | Sepetka et al. |
| 5,895,399 A | 4/1999 | Barbut |
| 5,908,407 A | 6/1999 | Frazee |
| 5,913,848 A | 6/1999 | Luther et al. |
| 5,916,208 A | 6/1999 | Luther et al. |
| 5,921,952 A | 7/1999 | Desmond, III et al. |
| 5,928,192 A | 7/1999 | Maahs |
| 5,935,122 A | 8/1999 | Fourkas et al. |
| 5,938,645 A | 8/1999 | Gordon |
| 5,957,882 A * | 9/1999 | Nita et al. ....................... 604/22 |
| 5,964,773 A | 10/1999 | Greenstein |
| 5,976,093 A | 11/1999 | Jang |
| 5,976,178 A | 11/1999 | Goldsteen et al. |
| 5,997,508 A | 12/1999 | Lunn et al. |
| 6,004,310 A | 12/1999 | Bardsley et al. |
| 6,013,085 A | 1/2000 | Howard |
| 6,022,336 A * | 2/2000 | Zadno-Azizi .......... A61B 17/22 604/101.05 |
| 6,022,340 A | 2/2000 | Sepetka et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoskia |
| 6,110,139 A | 8/2000 | Loubser |
| 6,139,524 A | 10/2000 | Killion |
| 6,146,370 A | 11/2000 | Barbut |
| 6,146,373 A | 11/2000 | Cragg et al. |
| 6,146,415 A | 11/2000 | Fitz |
| 6,152,909 A * | 11/2000 | Bagaoisan et al. ........... 604/523 |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,197,016 B1 | 3/2001 | Fourkas et al. |
| 6,206,868 B1 | 3/2001 | Parodi |
| 6,210,370 B1 | 4/2001 | Chi-Sing et al. |
| 6,234,971 B1 | 5/2001 | Jang |
| 6,254,628 B1 | 7/2001 | Wallace et al. |
| 6,258,080 B1 | 7/2001 | Samson |
| 6,277,139 B1 | 8/2001 | Levinson et al. |
| 6,270,477 B1 | 9/2001 | Bagaoisan |
| 6,287,319 B1 | 9/2001 | Aboul-Hosn et al. |
| 6,295,989 B1 | 10/2001 | Connors, III |
| 6,295,990 B1 | 10/2001 | Lewis |
| 6,306,106 B1 | 10/2001 | Boyle |
| 6,306,163 B1 | 10/2001 | Fitz |
| 6,364,900 B1 | 4/2002 | Heuser |
| 6,368,316 B1 | 4/2002 | Jansen et al. |
| 6,368,344 B1 | 4/2002 | Fitz |
| 6,379,325 B1 | 4/2002 | Benett et al. |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut |
| 6,428,531 B1 | 8/2002 | Visuri et al. |
| 6,435,189 B1 * | 8/2002 | Lewis et al. ................... 128/898 |
| 6,436,087 B1 | 8/2002 | Lewis et al. |
| 6,454,741 B1 | 9/2002 | Muni |
| 6,458,151 B1 | 10/2002 | Saltiel |
| 6,464,664 B1 | 10/2002 | Jonkman |
| 6,481,439 B1 | 11/2002 | Lewis et al. |

(56) References Cited

U.S. PATENT DOCUMENTS

| | | |
|---|---|---|
| 6,482,172 B1 | 11/2002 | Thramann |
| 6,482,217 B1 | 11/2002 | Pintor et al. |
| 6,508,824 B1 * | 1/2003 | Flaherty et al. ............. 606/185 |
| 6,517,520 B2 | 2/2003 | Chang et al. |
| 6,527,746 B1 | 3/2003 | Oslund et al. |
| 6,533,800 B1 | 3/2003 | Barbut |
| 6,540,712 B1 | 4/2003 | Parodi |
| 6,544,276 B1 | 4/2003 | Azizi |
| 6,549,800 B1 | 4/2003 | Atalar et al. |
| 6,551,268 B1 | 4/2003 | Kaganov et al. |
| 6,555,057 B1 | 4/2003 | Barbut et al. |
| 6,562,049 B1 | 5/2003 | Norlander et al. |
| 6,562,052 B2 | 5/2003 | Nobles et al. |
| 6,582,390 B1 | 6/2003 | Sanderson |
| 6,582,396 B1 | 6/2003 | Parodi |
| 6,582,448 B1 | 6/2003 | Boyle |
| 6,595,980 B1 | 7/2003 | Barbut |
| 6,605,074 B2 * | 8/2003 | Zadno-Azizi et al. ....... 604/509 |
| 6,595,953 B1 | 9/2003 | Coppi |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller |
| 6,641,573 B1 | 11/2003 | Parodi |
| 6,645,160 B1 | 11/2003 | Heesch |
| 6,645,222 B1 | 11/2003 | Parodi |
| 6,652,480 B1 | 11/2003 | Imran |
| 6,656,152 B2 | 12/2003 | Putz |
| 6,663,650 B2 | 12/2003 | Sepetka et al. |
| 6,663,652 B2 | 12/2003 | Daniel |
| 6,679,893 B1 | 1/2004 | Tran |
| 6,682,505 B2 | 1/2004 | Bates |
| 6,685,722 B1 | 2/2004 | Rosenbluth et al. |
| 6,702,782 B2 | 3/2004 | Miller |
| 6,711,436 B1 | 3/2004 | Duhaylongsod |
| 6,719,717 B1 | 4/2004 | Johnson |
| 6,730,104 B1 | 5/2004 | Sepetka et al. |
| 6,733,517 B1 | 5/2004 | Collins |
| 6,749,627 B2 | 6/2004 | Thompson et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,790,204 B2 | 9/2004 | Zadno-Azizi et al. |
| 6,824,545 B2 | 11/2004 | Sepetka et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,884,235 B2 | 4/2005 | McGuckin, Jr. et al. |
| 6,902,540 B2 * | 6/2005 | Dorros et al. .................... 604/8 |
| 6,905,490 B2 | 6/2005 | Parodi |
| 6,905,505 B2 | 6/2005 | Nash et al. |
| 6,908,474 B2 | 6/2005 | Hogendijk |
| 6,929,632 B2 | 8/2005 | Nita et al. |
| 6,929,634 B2 | 8/2005 | Dorros et al. |
| 6,936,060 B2 | 8/2005 | Hogendijk |
| 6,958,059 B2 | 10/2005 | Zadno |
| 6,960,189 B2 | 11/2005 | Bates et al. |
| 6,972,030 B2 | 12/2005 | Lee et al. |
| 7,001,400 B1 | 2/2006 | Modesitt et al. |
| 7,004,924 B1 | 2/2006 | Brugger |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 * | 4/2006 | Schonholz et al. ............ 606/200 |
| 7,033,336 B2 | 4/2006 | Hogendijk |
| 7,033,344 B2 | 4/2006 | Imran |
| 7,048,758 B2 | 5/2006 | Boyle |
| 7,063,714 B2 | 6/2006 | Dorros |
| 7,083,594 B2 | 8/2006 | Coppi |
| 7,104,979 B2 | 9/2006 | Jansen et al. |
| 7,108,677 B2 | 9/2006 | Courtney et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,169,165 B2 | 1/2007 | Belef et al. |
| 7,172,621 B2 | 2/2007 | Theron |
| 7,223,253 B2 | 5/2007 | Hogendijk |
| 7,232,452 B2 | 6/2007 | Adams |
| 7,250,042 B2 | 7/2007 | Kataishi et al. |
| 7,306,585 B2 | 12/2007 | Ross |
| 7,309,334 B2 | 12/2007 | von Hoffmann |
| 7,367,982 B2 | 5/2008 | Nash |
| 7,374,560 B2 | 5/2008 | Resseman et al. |
| 7,374,561 B2 | 5/2008 | Barbut |
| 7,384,412 B2 | 6/2008 | Coppi |
| 7,402,151 B2 | 7/2008 | Rosenman et al. |
| 7,422,579 B2 | 9/2008 | Wahr |
| 7,458,980 B2 | 12/2008 | Barbut |
| 7,497,844 B2 | 3/2009 | Spear et al. |
| 7,524,303 B1 | 4/2009 | Don Michael et al. |
| 7,534,250 B2 | 5/2009 | Schaeffer et al. |
| 7,731,683 B2 | 6/2010 | Jang et al. |
| 7,766,049 B2 | 8/2010 | Miller et al. |
| 7,766,820 B2 | 8/2010 | Core |
| 7,806,906 B2 | 10/2010 | Don Michael |
| 7,815,626 B1 | 10/2010 | McFadden et al. |
| 7,842,065 B2 | 11/2010 | Belef et al. |
| 7,867,216 B2 | 1/2011 | Wahr et al. |
| 7,905,856 B2 | 3/2011 | McGuckin, Jr. et al. |
| 7,905,877 B1 | 3/2011 | Jimenez et al. |
| 7,909,812 B2 | 3/2011 | Jansen et al. |
| 7,927,309 B2 | 4/2011 | Palm |
| 7,927,347 B2 | 4/2011 | Hogendijk et al. |
| 7,972,308 B2 | 7/2011 | Putz |
| 7,998,104 B2 | 8/2011 | Chang |
| 8,029,533 B2 | 10/2011 | Bagaoisan et al. |
| 8,052,640 B2 | 11/2011 | Fiorella et al. |
| 8,066,757 B2 | 11/2011 | Ferrera et al. |
| RE43,300 E | 4/2012 | Saadat et al. |
| 8,152,782 B2 | 4/2012 | Jang et al. |
| 8,157,760 B2 | 4/2012 | Criado et al. |
| 8,181,324 B2 | 5/2012 | McFadden et al. |
| 8,221,348 B2 | 7/2012 | Hackett et al. |
| 8,231,600 B2 | 7/2012 | von Hoffmann |
| 8,252,010 B1 | 8/2012 | Raju et al. |
| 8,343,089 B2 | 1/2013 | Chang |
| 8,414,516 B2 | 4/2013 | Chang |
| 8,545,552 B2 | 10/2013 | Garrison et al. |
| 8,574,245 B2 | 11/2013 | Garrison et al. |
| 8,870,805 B2 | 10/2014 | Chang |
| 2001/0044598 A1 | 11/2001 | Parodi |
| 2001/0049486 A1 | 12/2001 | Evans et al. |
| 2001/0049517 A1 | 12/2001 | Zadno |
| 2002/0087119 A1 | 7/2002 | Parodi |
| 2002/0128679 A1 * | 9/2002 | Turovskiy et al. ............ 606/200 |
| 2002/0133111 A1 | 9/2002 | Shadduck |
| 2002/0151922 A1 * | 10/2002 | Hogendijk et al. ........... 606/192 |
| 2002/0156455 A1 | 10/2002 | Barbut |
| 2002/0156460 A1 | 10/2002 | Ye et al. |
| 2002/0173815 A1 | 11/2002 | Hogenkijk |
| 2002/0183783 A1 | 12/2002 | Shadduck |
| 2003/0040762 A1 | 2/2003 | Dorros et al. |
| 2003/0065356 A1 | 4/2003 | Tsugita et al. |
| 2003/0069468 A1 | 4/2003 | Bolling |
| 2003/0078562 A1 | 4/2003 | Makower et al. |
| 2003/0186203 A1 | 10/2003 | Aboud |
| 2003/0212304 A1 | 11/2003 | Lattouf |
| 2003/0212384 A1 | 11/2003 | Hayden |
| 2004/0059243 A1 | 3/2004 | Flores et al. |
| 2004/0116878 A1 | 6/2004 | Byrd et al. |
| 2004/0133232 A1 | 7/2004 | Rosenbluth et al. |
| 2004/0210194 A1 | 10/2004 | Bonnette et al. |
| 2005/0004553 A1 | 1/2005 | Douk |
| 2005/0065467 A1 | 3/2005 | Pudelko et al. |
| 2005/0090802 A1 | 4/2005 | Connors et al. |
| 2005/0131453 A1 | 6/2005 | Parodi |

(56) References Cited

U.S. PATENT DOCUMENTS

| | | | |
|---|---|---|---|
| 2005/0154344 A1* | 7/2005 | Chang | 604/6.09 |
| 2005/0154349 A1 | 7/2005 | Renz | |
| 2005/0209559 A1 | 9/2005 | Thornton et al. | |
| 2005/0273051 A1 | 12/2005 | Coppi | |
| 2006/0058836 A1 | 3/2006 | Bose et al. | |
| 2006/0058837 A1 | 3/2006 | Bose et al. | |
| 2006/0058838 A1* | 3/2006 | Bose et al. | 606/200 |
| 2006/0089618 A1 | 4/2006 | McFerran et al. | |
| 2006/0135961 A1 | 6/2006 | Rosenman et al. | |
| 2006/0200191 A1 | 9/2006 | Zadno | |
| 2006/0271098 A1* | 11/2006 | Peacock, III | 606/200 |
| 2007/0021778 A1 | 1/2007 | Carly | |
| 2007/0073264 A1 | 3/2007 | Stedman et al. | |
| 2007/0173784 A1 | 7/2007 | Johansson et al. | |
| 2007/0197956 A1 | 8/2007 | Le et al. | |
| 2007/0198028 A1 | 8/2007 | Miloslavski et al. | |
| 2007/0198049 A1 | 8/2007 | Barbut | |
| 2008/0058839 A1* | 3/2008 | Nobles | A61B 17/0057 606/148 |
| 2008/0082107 A1* | 4/2008 | Miller et al. | 606/127 |
| 2008/0140010 A1 | 6/2008 | Kennedy et al. | |
| 2008/0177245 A1 | 7/2008 | Mesallum | |
| 2008/0200946 A1 | 8/2008 | Braun | |
| 2009/0018455 A1 | 1/2009 | Chang | |
| 2009/0024072 A1 | 1/2009 | Criado et al. | |
| 2009/0030400 A1 | 1/2009 | Bose et al. | |
| 2009/0198172 A1 | 8/2009 | Garrison et al. | |
| 2009/0254166 A1 | 8/2009 | Chou et al. | |
| 2009/0299393 A1 | 12/2009 | Martin et al. | |
| 2010/0004607 A1 | 1/2010 | Wilson et al. | |
| 2010/0030186 A1 | 2/2010 | Stivland | |
| 2010/0042118 A1 | 2/2010 | Garrison et al. | |
| 2010/0063479 A1 | 3/2010 | Merdan et al. | |
| 2010/0063480 A1 | 3/2010 | Shireman | |
| 2010/0094330 A1 | 4/2010 | Barbut | |
| 2010/0114017 A1 | 5/2010 | Lenker et al. | |
| 2010/0145308 A1 | 6/2010 | Layman et al. | |
| 2010/0185216 A1 | 7/2010 | Garrison et al. | |
| 2010/0204672 A1 | 8/2010 | Lockhart et al. | |
| 2010/0204684 A1 | 8/2010 | Garrison et al. | |
| 2010/0217276 A1 | 8/2010 | Garrison et al. | |
| 2010/0228269 A1 | 9/2010 | Garrison et al. | |
| 2010/0256600 A1 | 10/2010 | Ferrera | |
| 2010/0318097 A1 | 12/2010 | Ferrera et al. | |
| 2011/0009875 A1 | 1/2011 | Grandfield et al. | |
| 2011/0034986 A1 | 2/2011 | Chou et al. | |
| 2011/0112567 A1 | 5/2011 | Lenker et al. | |
| 2011/0125181 A1 | 5/2011 | Brady et al. | |
| 2011/0152760 A1 | 6/2011 | Parker | |
| 2011/0238041 A1 | 9/2011 | Lim et al. | |
| 2012/0109044 A1 | 5/2012 | Santamore et al. | |

FOREIGN PATENT DOCUMENTS

| | | |
|---|---|---|
| EP | 1440663 A1 | 7/2004 |
| JP | 2003-522560 A | 7/2003 |
| JP | 2005-500138 A | 1/2005 |
| WO | 95/05209 | 2/1995 |
| WO | 98/38930 | 9/1998 |
| WO | 99/45835 | 9/1999 |
| WO | 00/32266 | 8/2000 |
| WO | WO 00/76390 | 12/2000 |
| WO | WO-01/015767 A1 | 3/2001 |
| WO | 01/58365 | 8/2001 |
| WO | 02/32495 | 4/2002 |
| WO | WO-03/018085 A2 | 3/2003 |
| WO | WO 2003/090831 | 11/2003 |
| WO | 2004/006803 | 1/2004 |
| WO | 2005/051206 | 6/2005 |
| WO | 2008/144587 | 11/2008 |
| WO | 2009/012473 | 1/2009 |
| WO | 2009/099764 | 8/2009 |
| WO | 2009/100210 | 8/2009 |
| WO | WO 2010/075445 | 7/2010 |
| WO | WO-2010/075565 A2 | 7/2010 |
| WO | PCT/US12/49643 | 8/2012 |

OTHER PUBLICATIONS

Alexandrescu et al. (2006) "Filter-protected carotid stenting via a minimal cervical access with transitory aspirated reversed flow during initial passage of the target lesion" J. Endovasc. Ther. 13(2):196-204.

Alvarez et al. (2008). "Transcervical carotid stenting with flow reversal is safe in octogenarians: A preliminary safety study" J. Vasc. Surg. 47:96-100.

Bates M.D., et al. "Reversal of the Direction of Internal Carotid Artery Blood Flow by Occlusion of the Common and External Carotid Arteries in a Swine Model" Catherization and Cardiovascular Intervention 60:270-275 (2003).

Bates, M.D., et al. (2004) "Internal Carotid Artery Flow Arrest/Reversal Cerebral Protection Techniques" The West Virginal Medical Journal, vol. 99:60-63.

Bergeron et al. (1999). "Percutaneous stenting of the internal carotid artery: the European CAST I Study" J. Endovasc. Surg. 6:155-159.

Bergeron et al. (2008) MEET Presentation, Cannes, French Riviera "Why I do not use routine femoral access for CAS".

Bergeron P. et al. (1996) "Recurrent Carotid Disease: Will Stents be an alternative to surgery?" J Endovasc Surg; 3: 76-79.

Bourekas, E. C., A. P. Slivka, et al. (2004). "Intraarterial thrombolytic therapy within 3 hours of the onset of stroke." Neurosurgery 54(1): 39-44; discussion 44-6.

Chang, D.W., et al, "A new approach to carotid angioplasty and stenting with transcervical occlusion and protective shunting: Why it may be a better carotid artery intervention" (J Vasc Surg 2004; 39:994-1002.).

Chang, M.D., "Carotid Angioplasty and Stenting Using Transcervical Occlusion and Protective Shunting via a Mini Incision in the Neck: A New Technique for Difficult Femoral Access or Filter Placement May Be the Better Carotid Artery Intervention" 30th Global: Vascular and Endovascular Issues, Techniques and Horizons. XXVII 6.1-XXVII 6.2.

Coppi et al. (2005). "PRIAMUS Proximal flow blockage cerebral protection during cArotid stenting: Results from a multicenter Italian regiStry" J. Cardiovasc. Surg. 46:219-227.

Criado et al. (1997) "Evolving indications for and early results of carotid artery stenting" Am. J. Surg.; 174:111-114.

Criado et al. (2004). "Transcervical carotid artery angioplasty and stenting with carotid flow reversal: Surgical technique" J. Vasc. Surg. 18:257-261.

Criado et al. (2004). "Transcervical carotid stenting with internal carotid artery flow reversal: Feasibility and preliminary results" J. Vasc. Surg. 40:476-483.

Criado, et al. (2007). "Transcervical carotid stenting with carotid artery flow reversal: 3-year follow-up of 103 stents." J Vasc Surg 46(5): 864-9.

Criado, F.J., et al., Access strategies for carotid artery intervention. J Invasive Cardiol, 2000. 12(1): p. 61-8.

Criado, M.D., et al. (2004) "Carotid angioplasty with internal carotid artery flow reversal is well tolerated in the awake patient" Journal of Vascular Surgery, 40(1):92-7.

Diederich et al. (2004) "First Clinical experiences with an endovascular clamping system for neuroprotection during carotid stenting" Eur. J. Vasc. Endovasc. Surg. 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.

Feldtman, R. W., C. J. Buckley, et al. (2006). "How I do it: cervical access for carotid artery stenting." Am J Surg 192(6): 779-81.

Fiorella, D., M. Kelly, et al. (2008). "Endovascular Treatment of Cerebral Aneurysms." Endovascular Today June.

(56) References Cited

OTHER PUBLICATIONS

Frazee, J. G. and X. Luo (1999). "Retrograde transvenous perfusion." Crit Care Clin 15(4): 777-88, vii.
Frazee, J. G., X. Luo, et al. (1998). "Retrograde transvenous neuroperfusion: a back door treatment for stroke." Stroke 29(9): 1912-6.
Goldstein "Acute Ischemic Stroke Treatment in 2007" Circ 116:1504-1514 (2007).
Gray et al. (2007) "The CAPTURE registry: Results of carotid stenting with embolic protection in the post approval setting" Cath. Cardovasc. Interven. 69:341-348.
Henry et al. (1999) "Carotid stenting with cerebral protection: First clinical experience using the PercuSurge GuardWire System" J. Endovasc. Surg. 6:321-331.
Koebbe, C. J., E. Veznedaroglu, et al. (2006). "Endovascular management of intracranial aneurysms: current experience and future advances." Neurosurgery 59(5 Suppl 3): S93-102; discussion S3-13.
Lin et al. (2005) "Protected carotid artery stenting and angioplasty via transfemoral versus transcervical approaches" Vasc. Endovasc. Surg. 39(6):499-503.
Lo et al. (2005) "Advantages and indications of transcervical carotid artery stenting with carotid flow reversal" J. Cardovasc. Surg (Torino). 46(3):229-239.
Luebke, T et al. (2007) "Meta-analysis of randomized trials comparing carotid endarterectomy and endovascular treatment" Eur. J. Vasc. Endovasc. Surg. 34:470-479.
MacDonald, S. (2006) "Is there any evidence that cerebral protection is beneficial?" J. Cardiovasc. Surg. 47:127-36.
Mas et al. (2006) "Endarterectomy versus stenting in patients with symptomatic severe carotid stenosis" NEJM 355:1660-71.
Matas et al. (2007). "Transcervical carotid stenting with flow reversal protection: Experience in high-risk patients" J. Vasc. Surg. 46:49-54.
MO.MA Brochure; Proximal Flow Blockage Cerebral Protection Device—INVATEC.
MomaPresn (AET) 2002 Biamino, G; MO.MA as a distal protective device, University of Leipzig—Heart Center Department of Clinical and Interventional; Angiology Leipzig, Germany; 2002.
Nesbit, G. M., G. Luh, et al. (2004). "New and future endovascular treatment strategies for acute ischemic stroke." J Vasc Intery Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ohki, M.D., et al., "Efficacy of a proximal occlusion catheter with reversal of flow in the prevention of embolic events during carotid artery stenting: An experimental analysis" (J Vasc Surg 2001; 33:504-9).
Ouriel, K., R. K. Greenberg, et al. (2001). "Hemodynamic conditions at the carotid bifurcation during protective common carotid occlusion." J Vasc Surg 34(4): 577-80.
Parodi (2005). "Is flow reversal the best method of protection during carotid stenting?" J Endovasc. Ther. 12:166-170.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Perez-Arjona, E. A., Z. DelProsto, et al. (2004). "Direct percutaneous carotid artery stenting with distal protection: technical case report." Neurol Res 26(3): 338-41.
Pipinos et al. (2005). "Transcervical approach with protective flow reversal for carotid angioplasty and stenting" J. Endovasc. Ther. 12:446-453.
Pipinos et al. (2006). "Transcervical carotid stenting with flow reversal for neuroprotection: Technique, results, advantages, and limitations" 14(5):245-255.
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results froma prospective multicenter registry" J. Endovasc. Ther. 12:156-165.
Ribo et al. (2006). "Transcranial doppler monitoring of transcervical carotid stenting with flow reversal protection: a novel carotid revascularization technique" 27:2846-2849 (originally published online Sep. 28, 2006).
Ribo, M., C. Molina, et al. (2008). "Buying Time for Recanalization in Acute Stroke: Arterial Blood Infusion Beyond the Occluding Clot as a Neuroprotective Strategy." J Neuroimaging.
Ross, I. B. and G. D. Luzardo (2006). "Direct access to the carotid circulation by cut down for endovascular neuro-interventions." Surg Neurol 65(2): 207-11; discussion 211.
Stecker et al., (2002). "Stent placement in common carotid and internal carotid artery stenoses with use of an open transcervical approach in a patient with previous endarterectomy" J. Vasc. Interv. Radiol. 13:413-417.
Stejskal, et al., "Experience of 500 Cases of Neurophysiological Monitoring in Carotid Endarterectomy", Acta Neurochir, 2007, 149:681-689.
Theron, et al. "New Triple Coaxial Catheter System for Carotid Angioplasty with Cerebral Protection" AJNR 11:869-874, Sep./Oct. 1990 0195-6108/90/1106-0869 @ American Society of Neurology.
U.S. Appl. No. 12/633,730, filed Dec. 8, 2009, US2010-0185216.
U.S. Appl. No. 12/753,027, filed Apr. 1, 2010, US2010-0191169.
U.S. Appl. No. 12/753,039, filed Apr. 1, 2010, US2010-0191170.
U.S. Appl. No. 12/793,543, filed Jun. 3, 2010, US2011-0004147.
U.S. Appl. No. 13/017,905, filed Jan. 31, 2011, US2011-0125131.
U.S. Appl. No. 13/034,513, filed Feb. 24, 2011, US2011-0213459.
U.S. Appl. No. 13/566,451, filed Aug. 3, 2012.
U.S. Appl. No. 61/579,581, filed Dec. 22, 2011.
U.S. Appl. No. 61/681,584, filed Aug. 9, 2012.
PCT/US11/46775, Aug. 5, 2011, WO2012-021406.
U.S. Appl. No. 12/357,288, filed Jan. 21, 2009, US 2009-0198172.
U.S. Appl. No. 12/540,341, filed Aug. 12, 2009, US 2010-0042118.
U.S. Appl. No. 12/645,179, filed Dec. 22, 2009, US 2010-0217276.
U.S. Appl. No. 12/834,869, filed Jul. 12, 2010, US 2011-0034986.
U.S. Appl. No. 12/835,660, filed Jul. 13, 2010, US 2010-0280431.
U.S. Appl. No. 12/966,974, filed Dec. 13, 2010, US 2011-0082408.
U.S. Appl. No. 13/050,855, filed Mar. 17, 2011, US 2011-0166496.
U.S. Appl. No. 13/050,876, filed Mar. 17, 2011, US 2011-0166497.
PCT/US12/49643, Aug. 3, 2012, WO2013-022796.
U.S. Appl. No. 12/366,287, filed Feb. 5, 2009, US 2009-0254166.
U.S. Appl. No. 12/686,202, filed Jan. 12, 2010, US 2010-0204684.
U.S. Appl. No. 12/713,630, filed Feb. 26, 2010, US 2010-0228269.
U.S. Appl. No. 12/966,948, filed Dec. 13, 2010, US 2011-0087147.
U.S. Appl. No. 13/566,451, filed Aug. 3, 2012, US 2013-0035628.
U.S. Appl. No. 13/674,792, filed Nov. 12, 2012, US 2013-0172852.
U.S. Appl. No. 13/816,670, filed Feb. 12, 2013, US 2013-0197621.
U.S. Appl. No. 13/921,165, filed Jun. 18, 2013, US 2013-0281788.
U.S. Appl. No. 13/961,746, filed Aug. 7, 2013, US 2014-0046346.
U.S. Appl. No. 14/042,503, filed Sep. 30, 2013, US 2014-0031682.
U.S. Appl. No. 14/042,520, filed Sep. 30, 2013, US 2014-0031925.
U.S. Appl. No. 14/071,485, filed Nov. 4, 2013, US 2014-0058414.
U.S. Appl. No. 14/078,149, filed Nov. 12, 2013, US 2014-0135661.
U.S. Appl. No. 14/221,917, filed Mar. 21, 2014, US 2014-0296868.
U.S. Appl. No. 14/227,585, filed Mar. 27, 2014, US 2014-0296769.
U.S. Appl. No. 14/475,346, filed Sep. 2, 2014, US 2014-0371653.
U.S. Appl. No. 14/476,651, filed Sep. 3, 2014, US 2015-0080942.
U.S. Appl. No. 14/508,354, filed Oct. 7, 2014, US 2015-0025616.
U.S. Appl. No. 14/511,830, filed Oct. 10, 2014, US 2015-0141760.
U.S. Appl. No. 14/569,365, filed Dec. 12, 2014, US 2015-0174368.
U.S. Appl. No. 14/576,953, filed Dec. 19, 2014, US 2015-0173782.
U.S. Appl. No. 14/622,310, filed Feb. 13, 2015, US 2015-0150562.
PCT/US2013/054017, Aug. 7, 2013, WO 2014/025930.
PCT/US2013/069664, Nov. 12, 2013, WO 2014/078301.
PCT/US2014/031491, Mar. 21, 2014, WO 2014/160613.
PCT/US2014/032060, Mar. 27, 2014, WO 2014/160887.

(56) References Cited

OTHER PUBLICATIONS

PCT/US2014/042566, Jun. 16, 2014, WO 2014/204860.
PCT/US2014/071676, Dec. 19, 2014, WO 2015/100178.

* cited by examiner

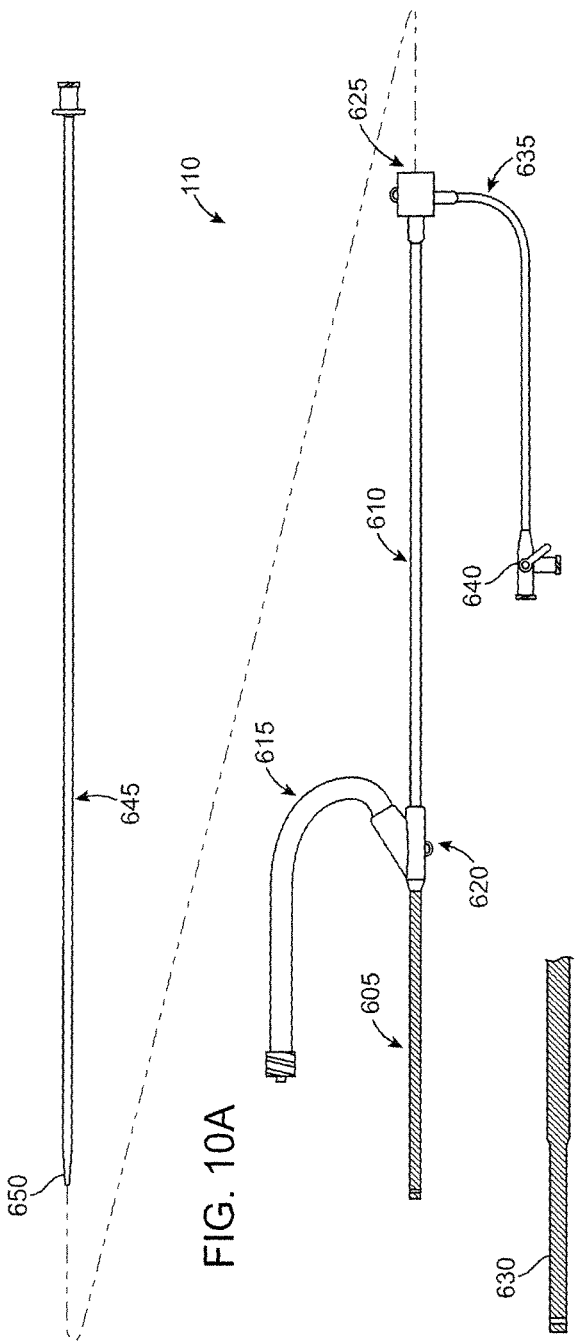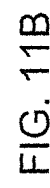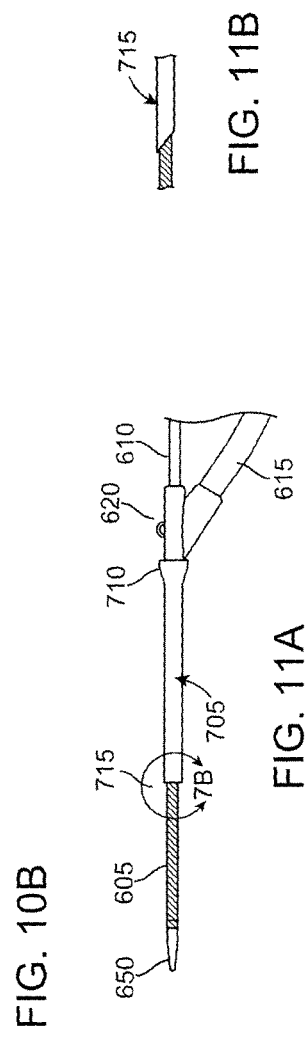

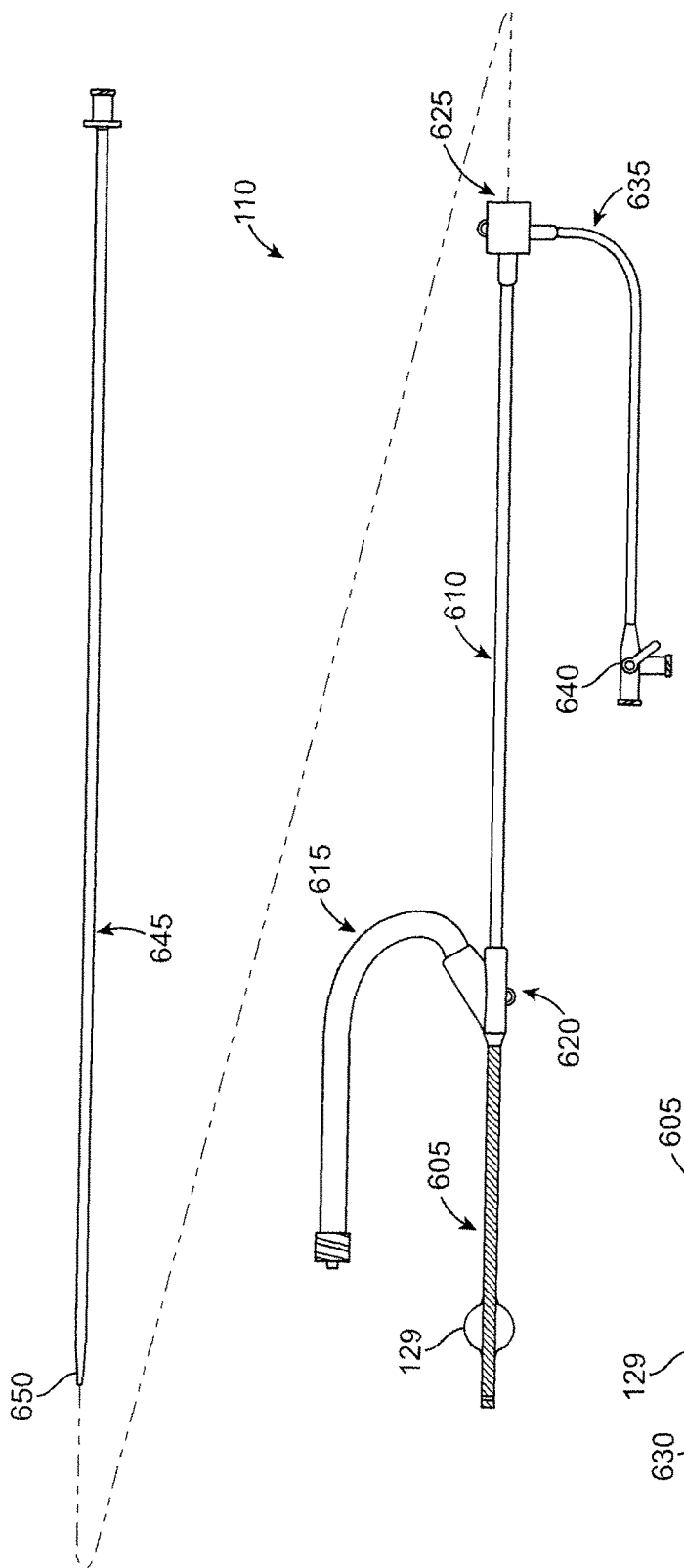
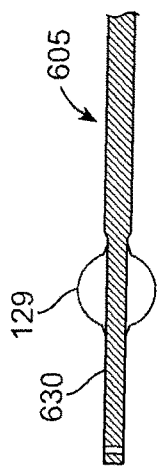
FIG. 12A
FIG. 12B

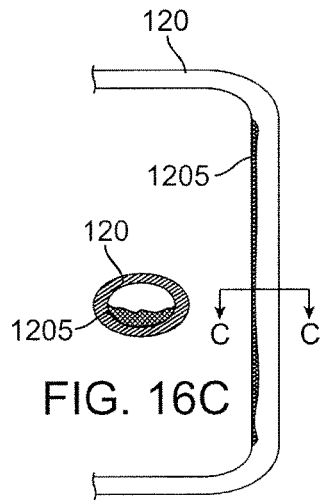
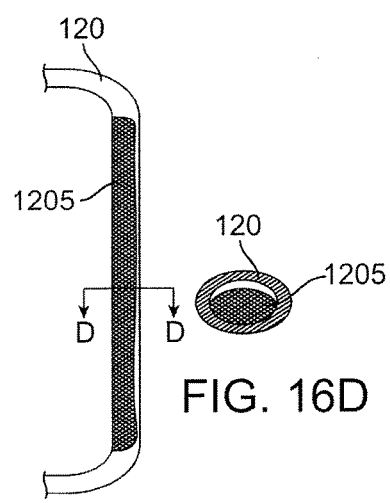
FIG. 16A   FIG. 16B
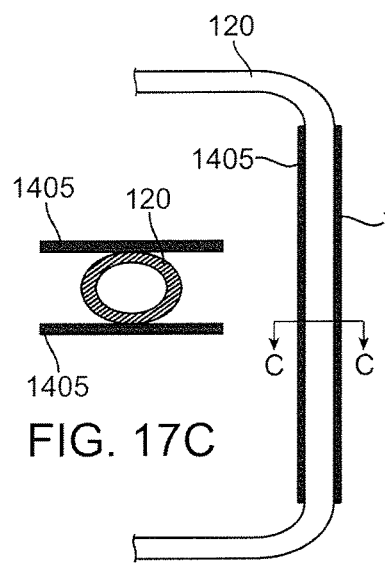
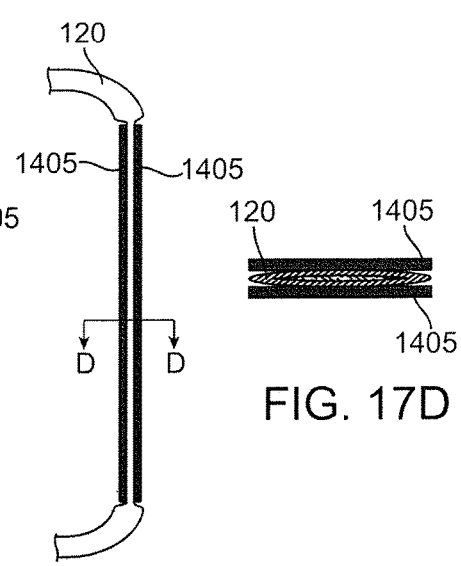
FIG. 17A   FIG. 17B

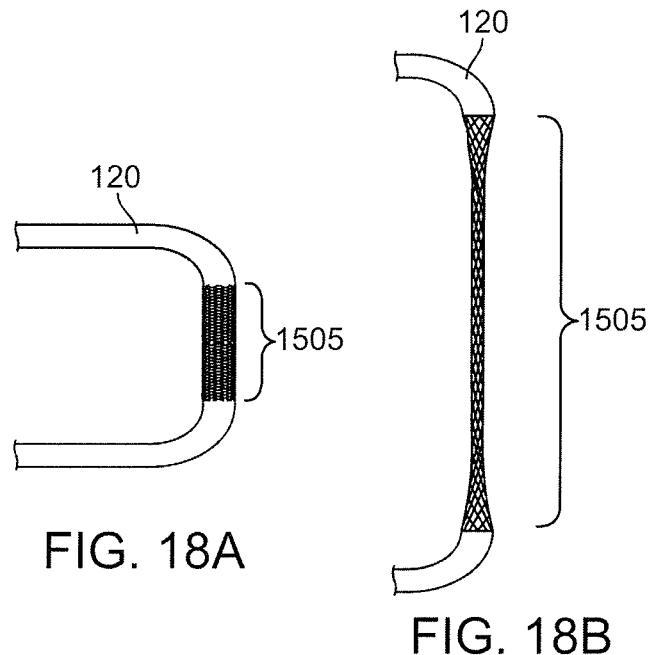
FIG. 18A
FIG. 18B
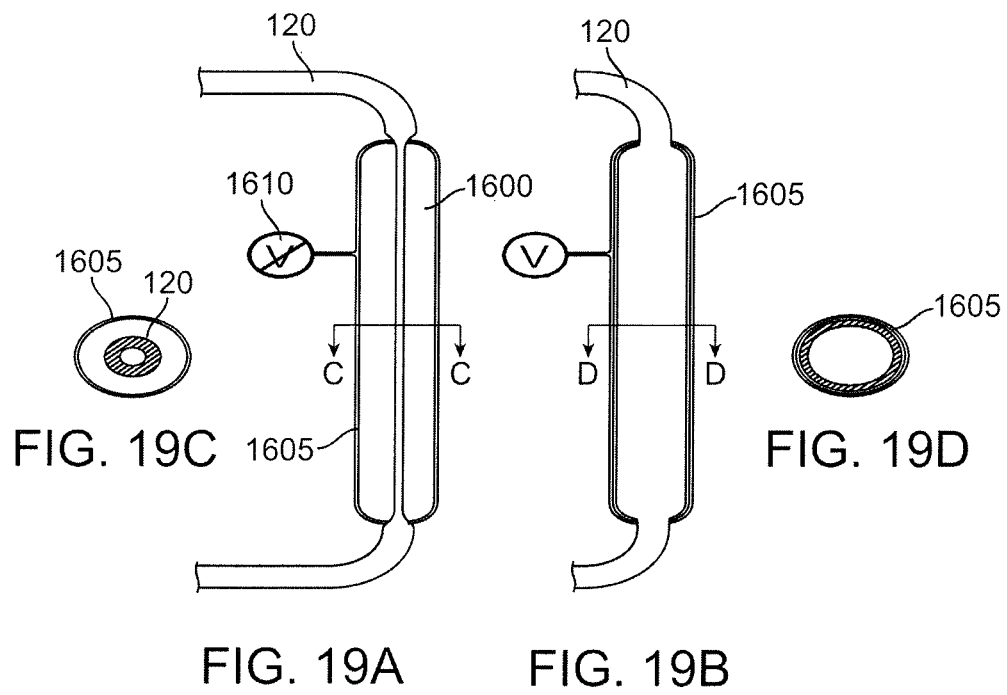
FIG. 19A
FIG. 19B
FIG. 19C
FIG. 19D

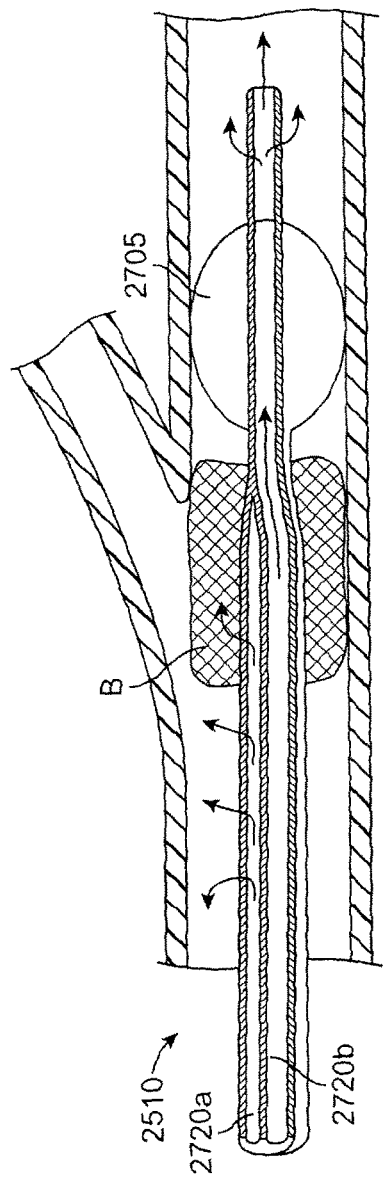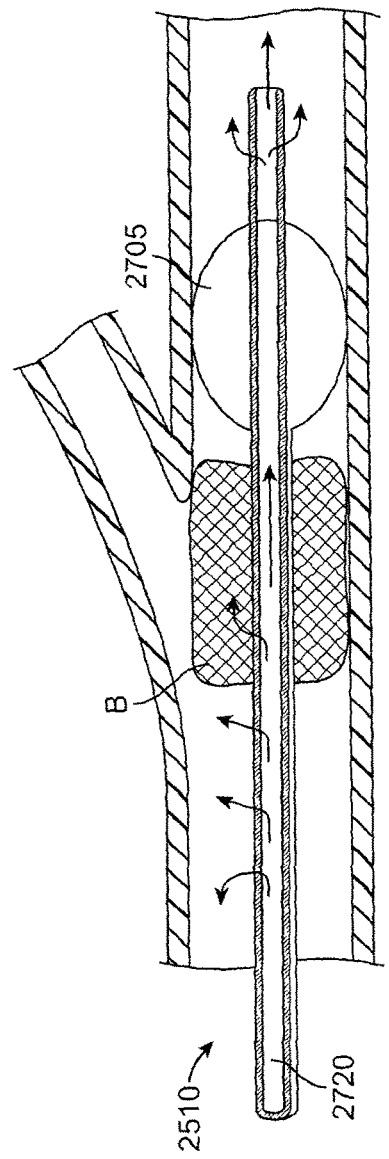

METHODS AND SYSTEMS FOR TREATMENT OF ACUTE ISCHEMIC STROKE

CROSS-REFERENCES TO PRIORITY DOCUMENTS

This application claims priority of U.S. Provisional Patent Application Ser. No. 61/140,601 filed on Dec. 23, 2008 and U.S. Provisional Patent Application Ser. No. 61/176,463 filed on May 7, 2009. Priority of the aforementioned filing dates is hereby claimed and the disclosures of the provisional patent applications are hereby incorporated by reference in their entirety.

BACKGROUND

The present disclosure relates generally to medical methods and devices. More particularly, the present disclosure relates to methods and systems for accessing the cerebral arterial vasculature and establishing retrograde blood flow during the interventional treatment of acute ischemic stroke.

Acute ischemic stroke is the sudden blockage of adequate blood flow to a section of the brain, usually caused by thrombus lodging or forming in one of the blood vessels supplying the brain. If this blockage is not quickly resolved, the ischemia may lead to permanent neurologic deficit or death. The timeframe for effective treatment of stroke is within 3 hours for IV thrombolytic therapy and 6 hours for site-directed intra-arterial thrombolytic therapy or interventional recanalization of a blocked cerebral artery. Reperfusing the ischemic brain after this time period has no overall benefit to the patient, and may in fact cause harm due to the increased risk of intracranial hemorrhage from fibrinolytic use. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death in the United States.

Endovascular treatment of acute stroke is comprised of either the intra-arterial administration of thrombolytic drugs such as recombinent tissue plasminogen activator (rtPA), or mechanical removal of the blockage, or often a combination of the two. As mentioned above, these interventional treatments must occur within hours of the onset of symptoms. Both IA thrombolytic therapy, and interventional thrombectomy involve accessing the blocked cerebral artery. Like IV thrombolytic therapy, IA thrombolytic therapy has the limitation in that it may take several hours of infusion to effectively dissolve the clot.

Mechanical therapies have involved either capturing and removing clot, dissolving the clot, or disrupting and suctioning the clot. The most widely used of these mechanical devices is the MERCI Retriever System (Concentric Medical, Redwood City, Calif.). This system uses a balloon guide catheter and a microcatheter to deliver a coiled retriever across the clot, and then during balloon occlusion and aspiration of the proximal vessel, pulling the retriever with the clot into the guide catheter. This device has had initially positive results as compared to thrombolytic therapy alone.

Other thrombectomy devices utilize expandable cages, baskets, or snares to capture and retrieve clot. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Frank suctioning of the clot has also been attempted using microcatheters and syringes, with mixed results. Devices which apply powered fluid vortices in combination with suction have been utilized to improve the efficacy of this method of thrombectomy. Finally, balloons and stents have been used to create a patent lumen through the clot when clot removal or dissolution was not possible.

Some Exemplary Issues with Current Technology

Interventions in the cerebral vasculature often have special access challenges. Most neurointerventional procedures use a transfemoral access to the carotid or vertebral artery and thence to the target cerebral artery. However, this access route is often tortuous and may contain stenosis plaque material in the aortic arch and carotid and brachiocephalic vessel origins, presenting a risk of embolic complications during the access portion of the procedure. In addition, the cerebral vessels are usually much narrower than coronary or other peripheral vasculature. In recent years, interventional devices such as wires, guide catheters, stents and balloon catheters, have all been scaled down and been made more flexible to better perform in the neurovascular anatomy. However, many neurointerventional procedures remain either more difficult or impossible because of device access challenges. In the setting of acute ischemic stroke where "time is brain," these extra difficulties may have a significant clinical impact.

Another challenge of neurointerventions is the risk of cerebral emboli. During the effort to remove or dissolve clot blockages in the cerebral artery, there is a significant risk of thrombus fragmentation creating embolic particles which can migrate downstream and compromise cerebral perfusion, leading to neurologic events. In carotid artery stenting procedures CAS, embolic protection devices and systems are commonly used to reduce the risk of embolic material from entering the cerebral vasculature. The types of devices include intravascular filters, and reverse flow or static flow systems. Unfortunately, because of the small anatomy and access challenges as well as the need for rapid intervention, these embolic protection systems are not used in interventional treatment of acute ischemic stroke. Some of the current mechanical clot retrieval procedures use aspiration as a means to reduce the risk of emboli and facilitate the removal of the clot. For example, the MERCI Retrieval System recommends attaching a large syringe to the guide catheter, and then blocking the proximal artery and aspirating the guide catheter during pull back of the clot into the guide. However, this step requires a second operator, may require an interruption of aspiration if the syringe needs to be emptied and reattached, and does not control the rate or timing of aspiration. This control may be important in cases where there is some question of patient tolerance to reverse flow. Furthermore, there is no protection against embolic debris during the initial crossing of the clot with the microcatheter and deployment of the retrieval device.

Another limitation of current systems is the difficulty in aspirating from the target artery only. Guide catheters are usually placed proximally in the carotid, vertebral or basilar artery below the blocked artery. Aspiration on the guide catheter pulls flow not just from the target artery but from other arteries branching off from the proximal artery. This reduces the suction force on the target artery and furthermore may reduce the level of blood flow to other tissue beds.

One severe drawback to current acute stroke interventions is the amount of time required to achieve recanalization, either during to access of the blocked cerebral artery, or time required to remove the blockage. Recanalization, either through thrombolytic therapy, mechanical thrombectomy, or other means, often takes hours during which time brain tissue is deprived of adequate oxygen. During this period, there is a risk of permanent injury to the brain tissue. Means to shorten the procedure time, and/or to provide oxygen to the brain tissue during the procedure, would reduce this risk.

SUMMARY

Disclosed are methods and devices that enable safe, rapid and relatively short and straight access to the cerebral arteries for the introduction of interventional devices to treat acute ischemic stroke. In addition, the disclosed methods and devices provide means to securely close the access site to the cerebral arteries to avoid the potentially devastating consequences of a transcervical hematoma. The methods and devices include a vascular access with retrograde flow system that can be used safely and rapidly in the neurointerventional procedures. The system offers the user a degree of blood flow control so as to address the specific hemodynamic requirements of the cerebral vasculature. The disclosed methods also include means to protect the cerebral penumbra during the procedure, to minimize injury to brain.

In one aspect, there is disclosed In one aspect, there is disclosed a system of devices for treating acute ischemic stroke, comprising: an arterial access sheath adapted to be introduced into a common carotid, internal carotid, or vertebral artery and receive blood from the artery; a shunt fluidly connected to the arterial access sheath, wherein the shunt provides a pathway for blood to flow from the arterial access sheath to a return site; a flow control assembly coupled to the shunt and adapted to regulate blood flow through the shunt; and a therapeutic device adapted to be introduced into the artery through the arterial access sheath and configured to treat a thrombotic blockage from a cerebral artery.

In another aspect, there is disclosed a system of devices for treating acute ischemic stroke, comprising: an arterial access sheath adapted to be introduced into a common carotid or vertebral artery and receive blood from the artery; a shunt fluidly connected to the arterial access sheath, wherein the shunt provides a pathway for blood to flow from the arterial access sheath to a return site; a flow control assembly coupled to the shunt and adapted to regulate blood flow through the shunt; and a perfusion catheter adapted to be introduced in into the artery through the arterial access sheath and positioned in a site adjacent to or through a thrombotic blockage in a cerebral artery, wherein the perfusion catheter has at least one perfusion lumen for perfusing fluid into the cerebral artery.

In another aspect, there is disclosed a method for accessing a cerebral artery to treat acute ischemic stroke, comprising: forming a penetration in a wall of a common carotid, internal carotid, or vertebral artery; positioning an arterial access sheath through the penetration into the artery; occluding at least one of the common or internal carotid artery or vertebral or basilar artery; and treating a thrombotic blockage in the cerebral artery.

In another aspect, there is disclosed a method for accessing a cerebral artery to treat acute ischemic stroke, comprising: forming a percutaneous penetration in a wall of a common carotid, internal carotid, or vertebral artery; applying a closure device at a site of penetration before placement of an arterial access sheath; positioning an arterial access sheath through the penetration into the artery; treating a thrombotic blockage in the cerebral artery; and closing the access site with the closure device.

In another aspect, there is disclosed a method for accessing a cerebral artery to treat acute ischemic stroke, comprising: forming a penetration in a wall of a common carotid, internal carotid or vertebral artery; positioning an arterial access sheath through the penetration; inserting a treatment device through the arterial access sheath into the artery; positioning at least a portion of the treatment device in the cerebral artery; removing thrombotic blockage in the cerebral artery using the treatment device.

In another aspect, there is disclosed a method for accessing a cerebral artery to treat acute ischemic stroke, comprising: forming a penetration in a wall of a common carotid or vertebral artery; positioning an arterial access sheath through the penetration; infusing a thrombolytic drug through the arterial access sheath to a thrombotic blockage in the cerebral artery; and removing thrombotic blockage in the cerebral artery using the thrombolytic drug.

In another aspect, there is disclosed a method for accessing a cerebral artery to treat acute ischemic stroke, comprising: forming a penetration in a wall of a common carotid or vertebral artery; positioning an arterial access sheath through the penetration; infusing a thrombolytic drug through the arterial access sheath to a thrombotic blockage in the cerebral artery; removing thrombotic blockage in the cerebral artery using the thrombolytic drug.

Other features and advantages should be apparent from the following description of various embodiments, which illustrate, by way of example, the principles of the invention.

BRIEF DESCRIPTION OF THE DRAWINGS

FIG. 10A illustrates an arterial access device useful in the methods and systems of the present disclosure.

FIG. 10B illustrates an additional arterial access device construction with a reduced diameter distal end.

FIGS. 11A and 11B illustrate a tube useful with the sheath of FIG. 10A.

FIG. 12A illustrates an additional arterial access device construction with an expandable occlusion element.

FIG. 12B illustrates an additional arterial access device construction with an expandable occlusion element and a reduced diameter distal end.

FIG. 16A-16D, FIGS. 17A-17D, FIGS. 18A and 18B, FIGS. 19A-19D, and FIGS. 20A and 20B, illustrate different embodiments of a variable flow resistance component useful in the methods and systems of the present disclosure.

FIGS. 27B-27C shows alternate embodiments of perfusion catheters.

DETAILED DESCRIPTION

Disclosed are methods and devices that enable safe, rapid and relatively short and straight access to the cerebral arteries for the introduction of interventional devices to treat acute ischemic stroke. In addition, the disclosed methods and devices provide means to securely close the access site to the cerebral arteries to avoid the potentially devastating consequences of a transcervical hematoma. The methods and devices include a vascular access with retrograde flow system that can be used safely and rapidly in the neurointerventional procedures. The system offers the user a degree of blood flow control so as to address the specific hemodynamic requirements of the cerebral vasculature. The disclosed methods also include means to protect the cerebral penumbra during the procedure, to minimize injury to brain.

Figure 1:
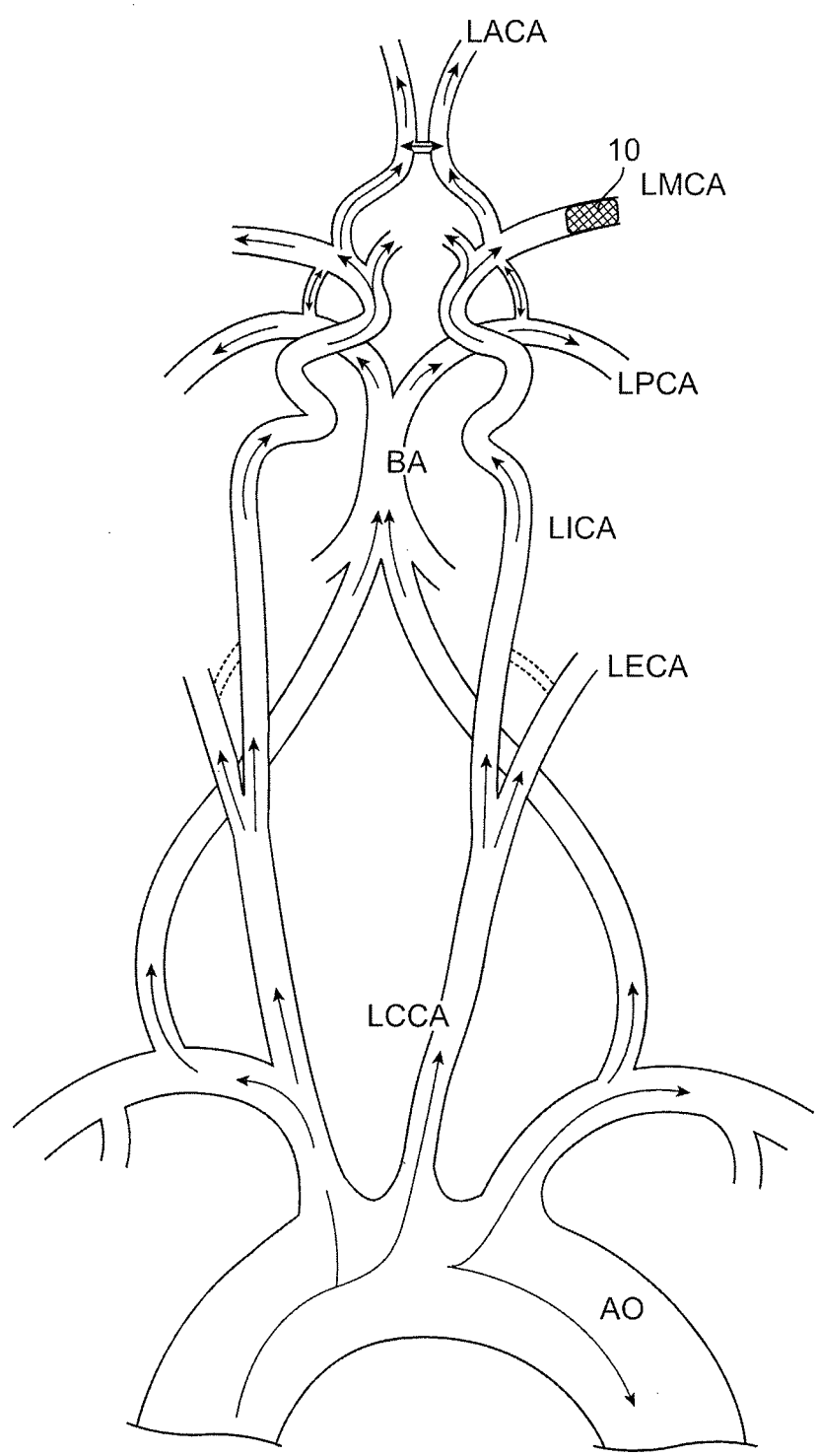
FIG. 1 schematically depicts normal, antegrade cerebral circulation with a thrombotic occlusion in the left middle cerebral artery.

FIG. 1 schematically depicts normal, antegrade cerebral circulation with a thrombotic occlusion 10 in the left middle cerebral artery RMCA. The left middle cerebral artery RMCA branches from the left internal carotid artery RICA. The middle cerebral arteries are large arteries that have tree-like branches that bring blood to the entire lateral aspect of each hemisphere of the brain. The thrombotic occlusion 10 occludes or limits blood flow through the left middle cerebral artery. Thus, blood supply to the brain is severely interrupted by the presence of the thrombotic occlusion 10 in the left middle cerebral artery, creating an ischemic stroke condition.

Figure 2:
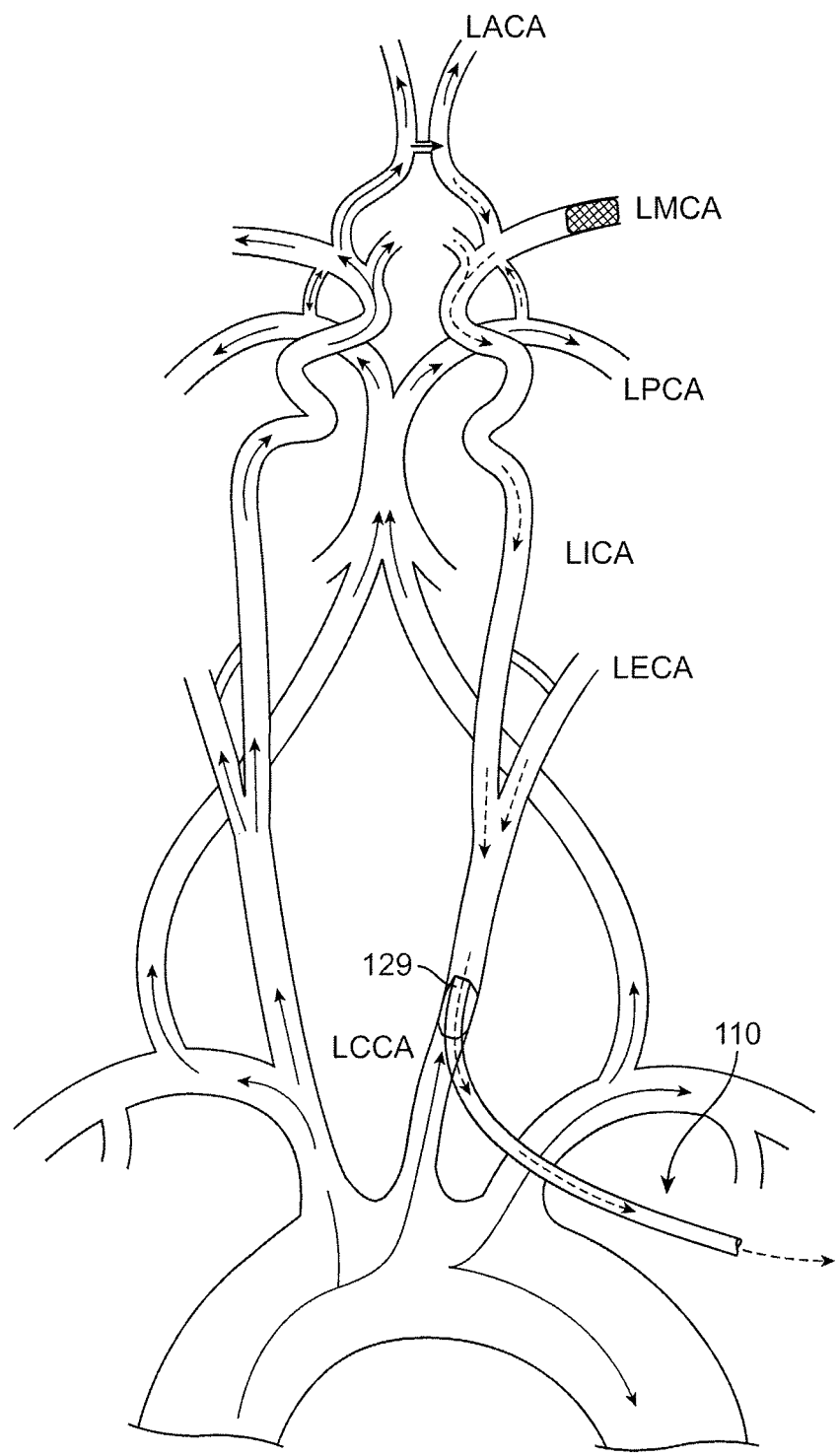
FIG. 2 depicts the blood flow circulation after retrograde flow has been established using the retrograde flow system described herein.

Pursuant to use of methods and systems described herein, a treatment method includes obtaining vascular access to the cerebral arteries and establishing retrograde flow in at least a portion of the cerebral circulation in order to safely treat the thrombotic occlusion. Retrograde flow is sometimes referred to as reverse flow. A mechanical thrombectomy device is inserted into the cerebral vasculature to remove the thrombotic occlusion under retrograde flow conditions, as described below. FIG. 2 depicts the blood flow circulation after retrograde flow has been established using the retrograde flow system described herein. The system includes an arterial access device 110 that enters the left common carotid artery LCCA to provide access to the cerebral vasculature. An expandable occlusion element 129 on the arterial access device 110 can be used to occlude an artery in the cerebral vasculature and establish retrograde flow, as described more fully below. Various arteries may be occluded including, for example, the common carotid artery, internal carotid artery, and/or vertebral artery. Exemplary embodiments of the system and its components are described in detail below.

Figure 3:
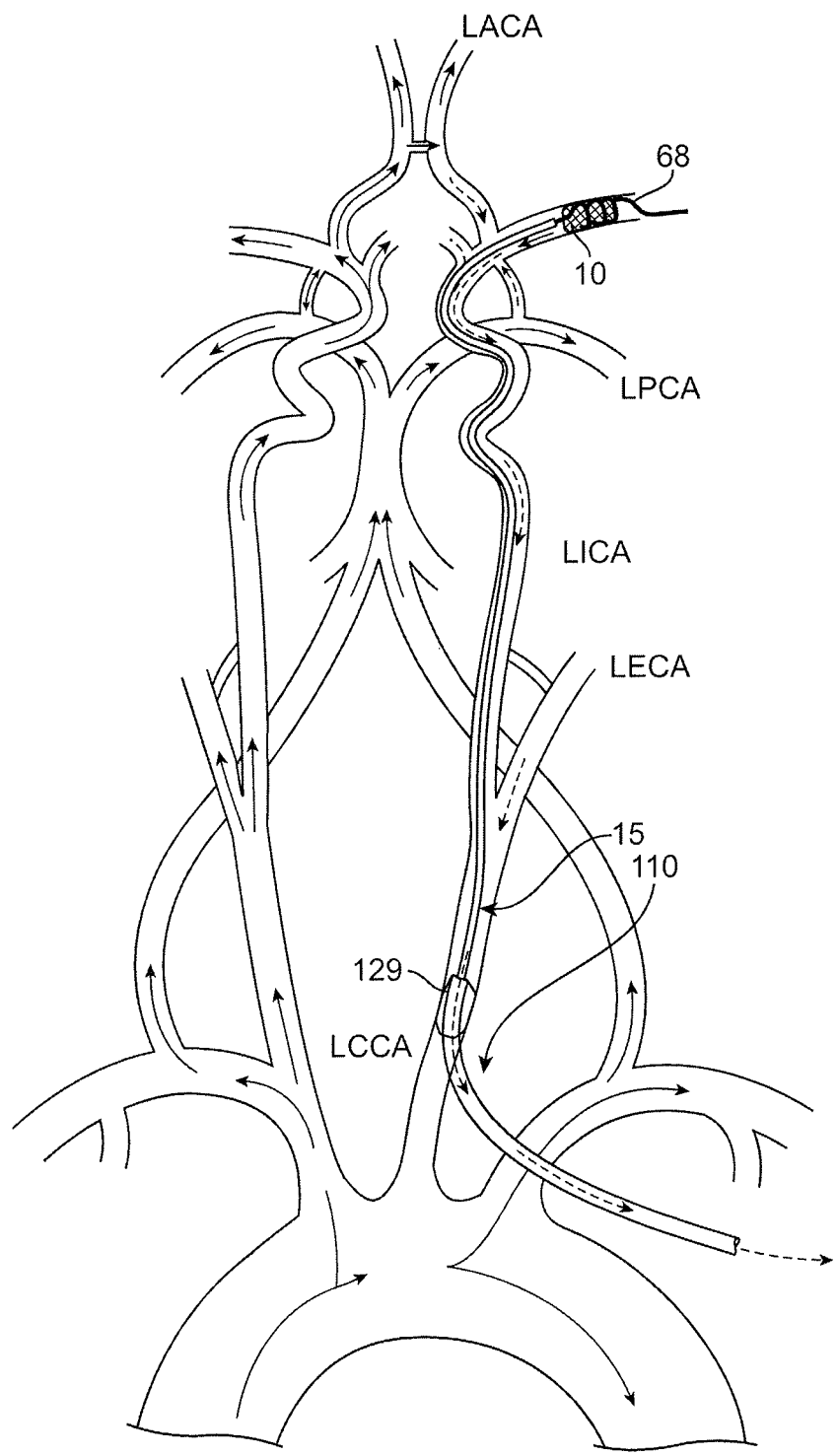
FIG. 3 shows the cerebral vasculature with a mechanical thrombectomy device inserted through an exemplary arterial access device.

FIG. 3 shows the cerebral vasculature with a mechanical thrombectomy device 15 inserted through the arterial access device 110. The thrombectomy device 15 includes an elongate catheter that can be advanced through the arterial access device 110 to the location of the thrombotic occlusion 10. The thrombectomy device 15 has a distal region that includes a thrombus engaging element 68 that is adapted to interact with and remove the thrombotic occlusion 10, as described more fully below. Various embodiments of the thrombectomy device 15 are described below.

Figure 4:
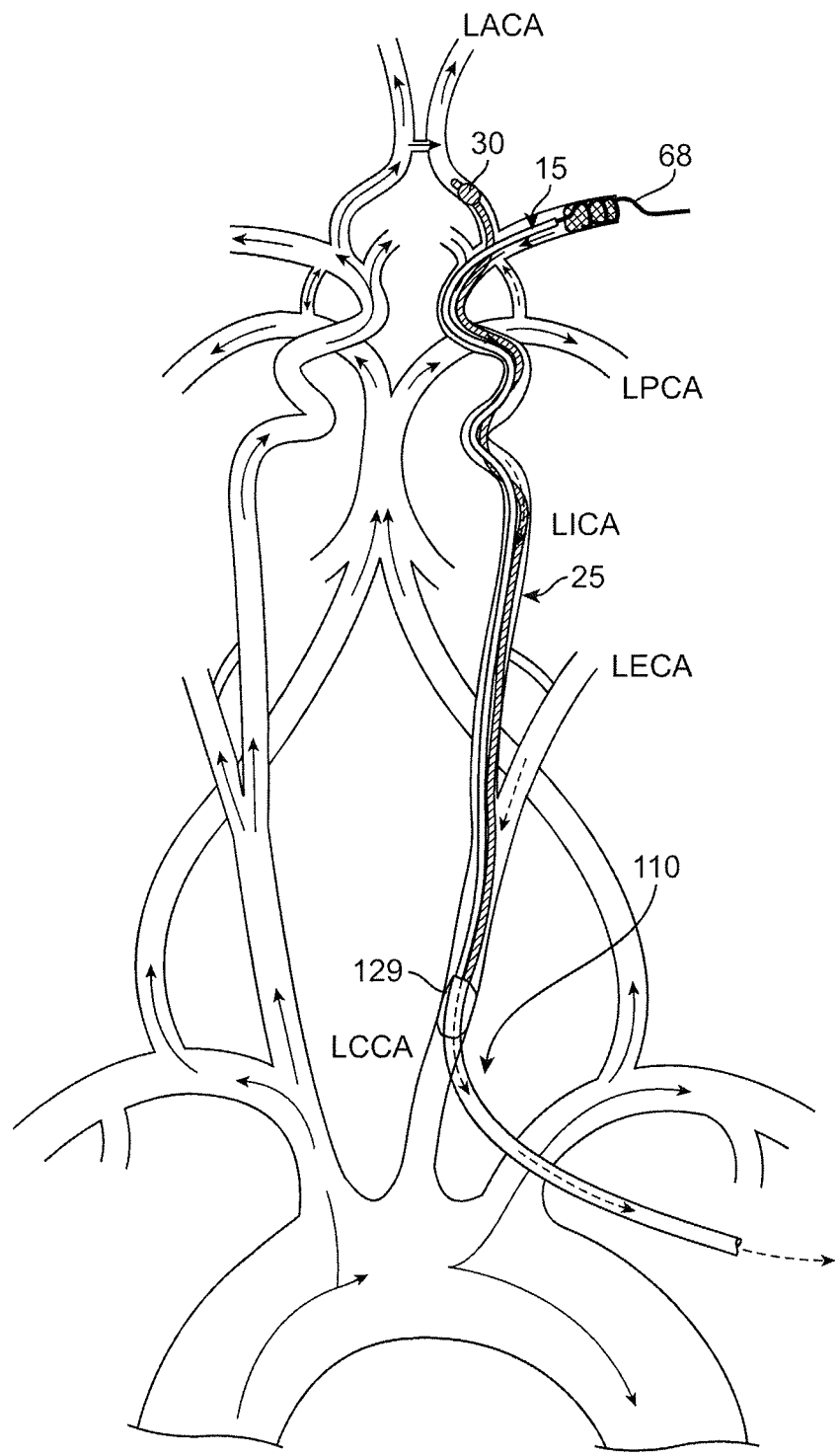
FIG. 4 shows an alternate embodiment wherein a secondary interventional device is advanced through the arterial access device and into a collateral cerebral artery.

FIG. 4 shows an alternate embodiment wherein a secondary interventional device, such as a balloon catheter 25, is advanced through the arterial access device 110 and into a collateral cerebral artery such as the anterior cerebral artery ACA. The balloon catheter 25 includes an expandable balloon 30 that can be expanded in the collateral cerebral artery to occlude that artery. Occlusion of the collateral cerebral artery enhances suction and reverse flow through the cerebral vasculature, as described in detail below.

Figure 5A:
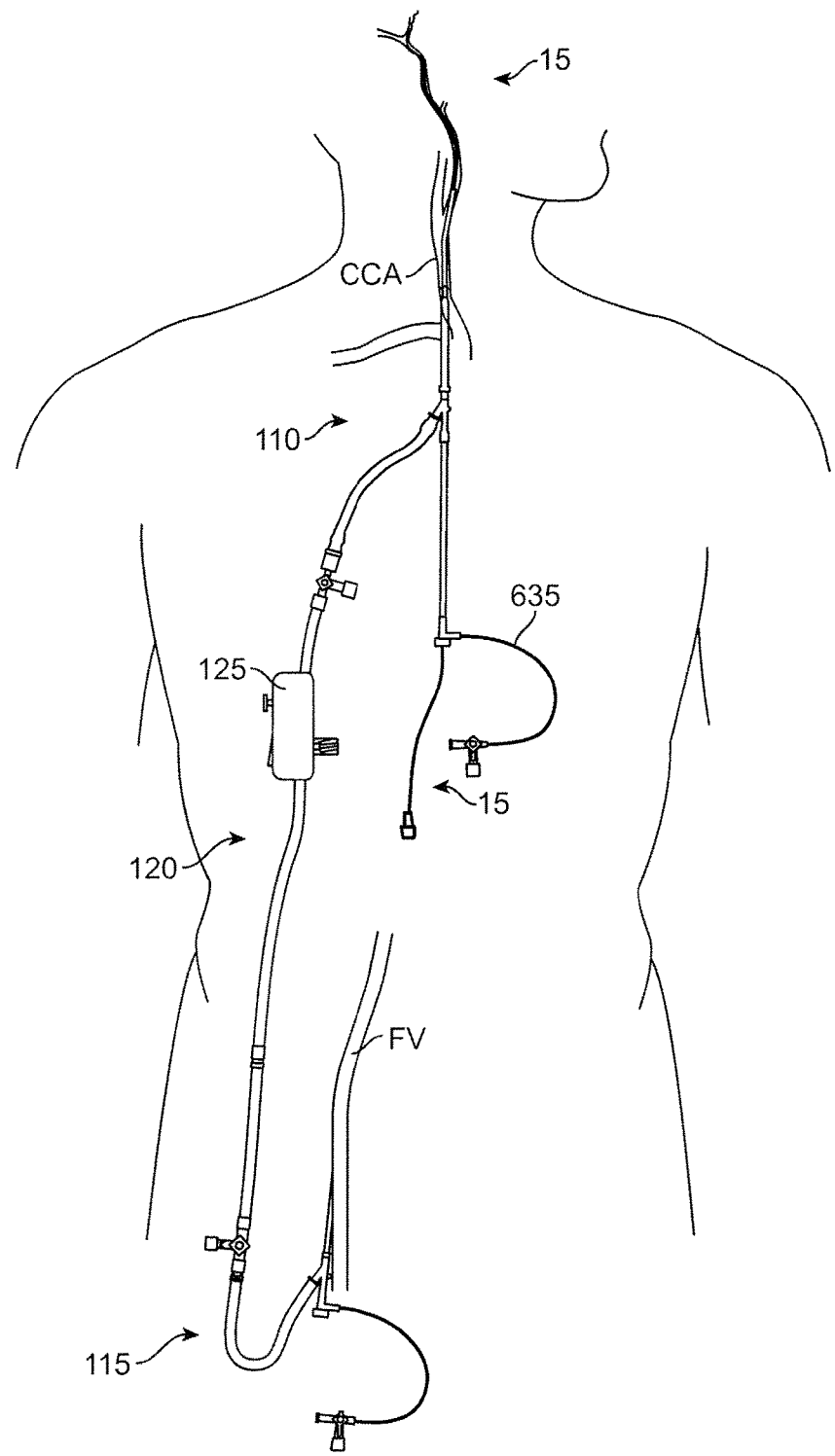
FIG. 5A shows an exemplary embodiment of a vascular access and reverse flow system that can be used to establish retrograde flow during removal of the thrombotic occlusion.

FIG. 5A shows an exemplary embodiment of a vascular access and reverse flow system 100 that can be used to establish retrograde flow during removal of the thrombotic occlusion 10. The system 100 includes the arterial access device 110, a venous return device 115, and a shunt 120 that provides a passageway for retrograde flow from the arterial access device 110 to the venous return device 115. A flow control assembly 125 interacts with the shunt 120. The flow control assembly 125 is adapted to regulate and/or monitor the retrograde flow through the shunt 120, as described in more detail below. The flow control assembly 125 interacts with the flow pathway through the shunt 120, either external to the flow path, inside the flow path, or both.

Figure 5B:
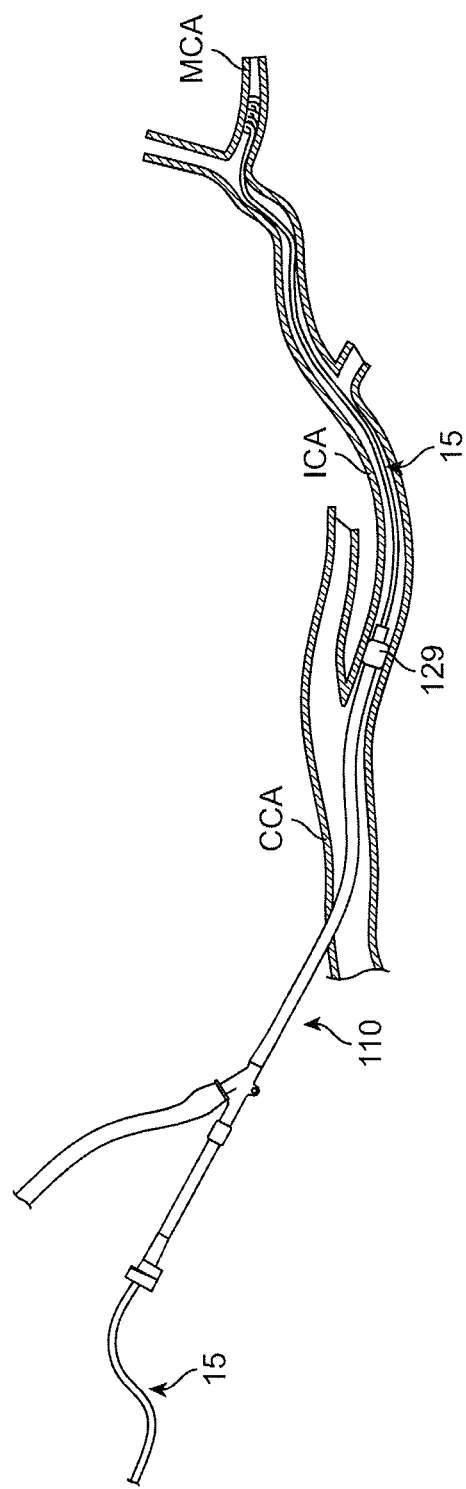
FIG. 5B shows an enlarged view of the common carotid artery, internal carotid artery, and middle cerebral artery with an arterial access device and a thrombectomy device deployed.

In an embodiment, the arterial access device 110 at least partially inserts into the common carotid artery CCA and the venous return device 115 at least partially inserts into a venous return site, such as the femoral vein or internal jugular vein, as described in more detail below. The venous return device 115 can be inserted into the femoral vein FV via a percutaneous puncture in the groin. The arterial access device 110 and the venous return device 115 couple to opposite ends of the shunt 120 at connectors. As shown in FIG. 5B, the distal end of the arterial access device 110 with the occlusion element 129 may be positioned in the ICA. Alternately, in some circumstances where the ICA access is extremely tortuous, it may be preferable to position the occlusion element more proximally in the common carotid artery. When flow through the internal carotid artery is blocked (using the occlusion element 129), the natural pressure gradient between the internal carotid artery and the venous system causes blood to flow in a retrograde or reverse direction from the cerebral vasculature through the internal carotid artery and through the shunt 120 into the venous system. The flow control assembly 125 modulates, augments, assists, monitors, and/or otherwise regulates the retrograde blood flow.

The thrombectomy device 15 is deployed into the left middle cerebral artery through the arterial access device and via the internal carotid artery. A distal region of the thrombectomy device 15 is positioned in the middle cerebral artery in interaction with the thrombotic occlusion. A proximal region of the thrombectomy device 15 protrudes from an access port in the arterial access device 110. This is described in more detail with reference to FIG. 5B, which shows an enlarged view of the common carotid artery CCA, internal carotid artery ICA, and middle cerebral artery MCA with the arterial access device 110 and the thrombectomy device 15 deployed. The arterial access device 110 accesses the common carotid artery via a transcervical approach such as via a direct cut down to the common carotid artery CCA or a percutaneous puncture of the CCA. The thrombectomy device 15 gains access to the internal carotid artery ICA via insertion through an internal lumen of the arterial access device 110, such as by being inserted into a hemostasis valve that provides access into the arterial access device 110. As mentioned, the arterial access device 110 can include an occlusion element 129 that occludes the internal or common carotid artery. An exemplary manner in which the thrombectomy device 15 removes the thrombotic occlusion is described in detail below.

As discussed, the arterial access device 110 provides access to the anterior and middle cerebral arteries via the common carotid artery CCA using a transcervical approach. Transcervical access provides a short length and non-tortuous pathway from the vascular access point to the target treatment site thereby easing the time and difficulty of the procedure, compared for example to a transfemoral approach. Additionally, this access route reduces the risk of emboli generation from navigation of diseased, angulated, or tortuous aortic arch or common carotid artery anatomy. In another embodiment, the arterial access device provides access to the basilar artery BA or posterior cerebral arteries PCA via a cut down incision to in the vertebral artery or a percutaneous puncture of the vertebral artery.

In an embodiment, transcervical access to the common carotid artery is achieved percutaneously via an incision or puncture in the skin through which the arterial access device 110 is inserted. If an incision is used, then the incision can be about 0.5 cm in length. An occlusion element 129, such as an expandable balloon, can be used to occlude the internal carotid artery ICA or the common carotid artery CCA at a location proximal of the distal tip of the arterial access device 110. The occlusion element 129 can be located on the arterial access device 110 or it can be located on a separate device. In an alternate embodiment, the arterial access device 110 accesses the common carotid artery CCA via a direct surgical transcervical approach. In the surgical approach, the common carotid artery can be occluded using a tourniquet.

In another embodiment, the arterial access device 110 accesses the common carotid artery CCA via a transcervical approach while the venous return device 115 access a venous return site other than the femoral vein, such as the internal jugular vein. In another embodiment, the system provides retrograde flow from the carotid artery to an external receptacle rather than to a venous return site. The arterial access device 110 connects to the receptacle via the shunt 120, which communicates with the flow control assembly 125. The retrograde flow of blood is collected in the receptacle 130. If desired, the blood could be filtered and subsequently returned to the patient. The pressure of the receptacle 130 could be set at zero pressure (atmospheric pressure) or even lower, causing the blood to flow in a reverse direction from the cerebral vasculature to the receptacle 130. Optionally, to achieve or enhance reverse flow from the internal carotid artery, flow from the external carotid artery can be blocked, typically by deploying a balloon or other occlusion element in the external carotid artery just above the bifurcation with the internal carotid artery.

In another embodiment, reverse flow may be replaced or augmented by application of an aspiration source to a port 131 (such as a stopcock) that communicates with the flow shunt 120. Examples of an aspiration source include a syringe, pump, or the like. Alternately, the system may include an active pump as part of the flow control assembly 125, with controls for pump flow rate and/or flow monitoring included in the assembly.

In yet another embodiment, the system may be used to deliver intra-arterial thrombolytic therapy, such as through a sidearm in the arterial access device 110. For example, thrombolytic therapy may be infused to the thrombotic occlusion 10 through the arterial access device 110 via a flush line 635. In another embodiment, the system may be used to deliver intra-arterial thrombolytic therapy via a micro catheter which is inserted into the arterial access device 110. The micro catheter is delivered to the site of the thrombotic occlusion 10 to infuse a thrombolytic drug. The thrombolytic therapy may be delivered either in conjunction with or as an alternative to mechanical thrombectomy such as the thrombectomy device 15.

In another embodiment, the system 100 may include a means to perfuse the cerebral vasculature and ischemic brain tissue via a perfusion catheter delivered, for example, through the arterial access device 110 to a site distal to the thrombotic occlusion 10. The perfusion catheter is adapted to deliver a perfusion solution to a desired location. Perfusion solution may include, for example, autologous arterial blood, either from the AV shunt 120 or from another artery, oxygenated solution, or other neuroprotective agents. In addition, the perfusion solution may be hypothermic to cool the brain tissue, another strategy which has been shown to minimize brain injury during periods of ischemia. The perfusion catheter may also be used to deliver a bolus of an intra-arterial thrombolytic agent pursuant to thrombolytic therapy. Typically, thrombolytic therapy may take up to 1-2 hours or more to clear a blockage after the bolus has been delivered. Mechanical thrombectomy may also take up to 1 to 2 hours to successfully recanalize the blocked artery. Distal perfusion of the ischemic region may minimize the level of brain injury during the stroke treatment procedure.

Another embodiment of the system 100 includes a means for retroperfusion of the cerebral vasculature during the acute stroke treatment procedure. Cerebral retroperfusion as described by Frazee et al involves selective cannulation and occlusion of the transverse sinuses via the internal jugular vein, and infusion of blood via the superior sagittal sinus to the brain tissue, during treatment of ischemic stroke. The following articles, which are incorporated herein by reference in their entirety, described cerebral retroperfusion and are incorporated by reference in their entirety: Frazee, J. G. and X. Luo (1999). "Retrograde transvenous perfusion." Crit Care Clin 15(4): 777-88, vii.; and Frazee, J. G., X. Luo, et al. (1998). "Retrograde transvenous neuroperfusion: a back door treatment for stroke." Stroke 29(9): 1912-6. This perfusion, in addition to providing protection to the cerebral tissue, may also cause a retrograde flow gradient in the cerebral arteries. Used in conjunction with the reverse flow system 100, a retroperfusion component may provide oxygen to brain tissue, as well as aid in capture of embolic debris into the reverse flow shunt during recanalization of the thrombotic occlusion 10.

EXEMPLARY EMBODIMENTS OF THROMBECTOMY DEVICE

Figure 6:
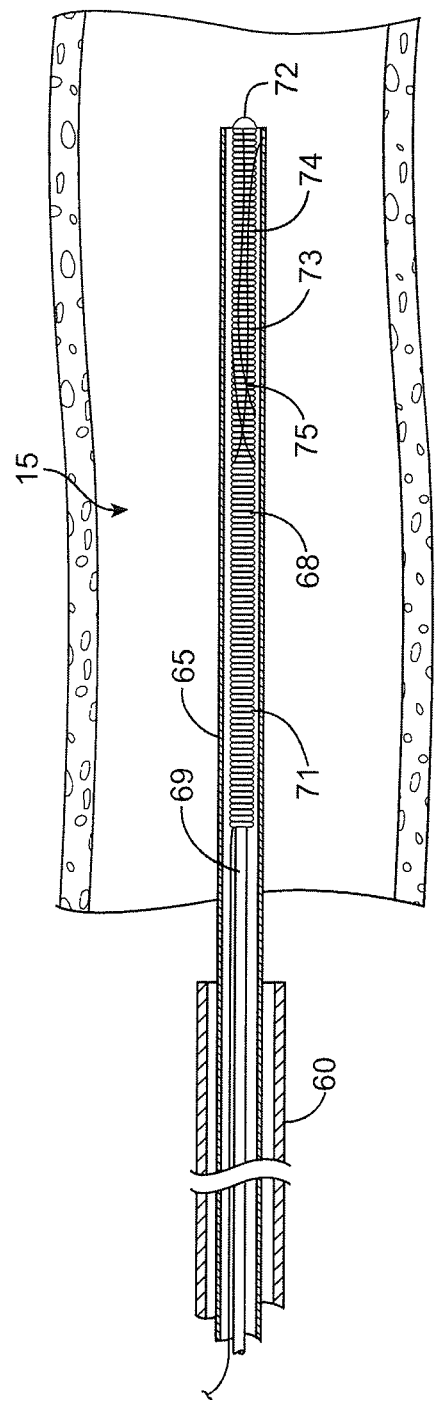
FIG. 6 shows an enlarged view of a distal region of an exemplary thrombectomy device in a collapsed condition in a blood vessel.

FIG. 6 shows an enlarged view of a distal region of an exemplary thrombectomy device 15 in a collapsed condition in a blood vessel such as the left middle cerebral artery. As discussed, the distal end of the thrombectomy device 15 is advanced to the left middle cerebral artery and the thrombotic occlusion 10 through the arterial access device 110. The thrombectomy device 15 may include a microcatheter 60 to assist in delivering the device into the distal vasculature The thrombectomy device 15 has a thrombus engaging element 68 extending from an insertion element 69 comprised of an elongate body. The engaging element has a coiled or substantially-coiled configuration that engages the thrombotic occlusion as described below. Exemplary embodiments of the engaging element are described below although it should be appreciated that the configuration of the engaging element 68 may vary. The engaging element 68 is movable from a collapsed position (shown in FIG. 6) to an expanded position (shown in FIGS. 7 and 8). When the engaging element 68 is contained within a sheath 65 or microcatheter 60, the engaging element 68 is in a relatively straight configuration. The engaging element 68 has a distal portion 70 (FIG. 7), which forms a relatively closed structure, which can catch or trap the obstruction, or any part thereof, to prevent migration of the obstruction or part thereof. The engaging element 68 has a proximal portion 71 (FIG. 8) which is formed with smaller coils than the distal portion 70. The proximal portion 71 engages the thrombotic occlusion as described below.

The engaging element 68 may have a number of markers which provide an indication as to how much of the engaging element 68 extends from the sheath 65 or microcatheter 60. For example, markers may indicate when the engaging element 68 is ½, ¾ or fully exposed. In this manner, the user may quickly advance the engaging element 68 through the sheath 65 or microcatheter 60 without inadvertently exposing and advancing the engaging element 68 out of the sheath 65 or microcatheter. The markers can also be used to provide a controlled diameter of the engaging element 68 since the diameter of the engaging element 68 is known for the various positions corresponding to the markers. The markers may also be used to size the vessel in which the engaging element 68 is positioned by observing when the engaging element 68 engages the vessel walls and determining the size of the engaging element 68 using the markers.

The insertion element 69 can be made, for example, of a superelastic material or stainless steel having a diameter of 0.004 to 0.038 inch and preferably about 0.010 inch. Although the insertion element 69 can be a solid, elongate element, the insertion element 69 may take any other suitable structure such as a hollow tube. The engaging element 68 can be made of a superelastic material, such as nitinol, and has a diameter of 0.005-0.018 inch, more preferably 0.005-0.010 inch and most preferably about 0.008 inch. The engaging element 68 may have a rounded, atraumatic tip 72 to prevent damage to the vessel and facilitate advancement through the vessel, microcatheter 60 and/or sheath 65. A radiopaque wire 73, such as platinum ribbon 74 having a width of 0.004 inch and a thickness of 0.002 inch, may be wrapped around the engaging element 68 to improve radiopacity.

The thrombectomy device 15 can be self-expanding but may also be expanded with an actuator. The actuator can be a thin filament which is tensioned to move the thrombectomy device 15 to the expanded position.

The thrombectomy device 15 may also include a cover 75 which extends between adjacent coils. The cover 75 may be a number of individual strands which extend between the coils or may be an elastic membrane which covers the coils. The thrombectomy device 15 may also include a flush lumen and/or an aspiration lumen.

It should be appreciated that the thrombectomy device 15 is not limited to the specific embodiments described above and that other embodiments of thrombectomy devices or therapeutic devices may also be used. For example, the device may be an expandable cage, basket, snare, or grasper which is used to capture and remove the thrombotic blockage. The device may also be a clot disruption device, which may be used to break up the thrombus for easier aspiration and removal. The clot disruption device may be, for example, a mechanical disrupter, sonic or ultrasonic energy source, or other energy source, or a hydraulic or vortex energy source, to break up the clot. The thrombectomy device may also comprise a aspiration means to remove the thrombotic blockage.

Other means for providing flow through a thrombotic blockage include recanalizing means, for example delivering a balloon catheter and dilating a passage through the blockage, or deploying a stent through the thrombotic blockage to create a lumen through the blockage. A stent device may be a permanent implantable stent or may be a temporary stent to open up the blocked passage for a period of time before being retrieved. The blockage may be removed by the stent or by some other thrombectomy means. Both thrombectomy and recanalization devices may be used in conjunction with thrombolytic infusion. Some exemplary stent-related devices and methods are described in the following U.S. patents, which are incorporated herein by reference in their entirety: U.S. Pat. No. 5,964,773 and U.S. Pat. No. 5,456,667.

Figure 7:
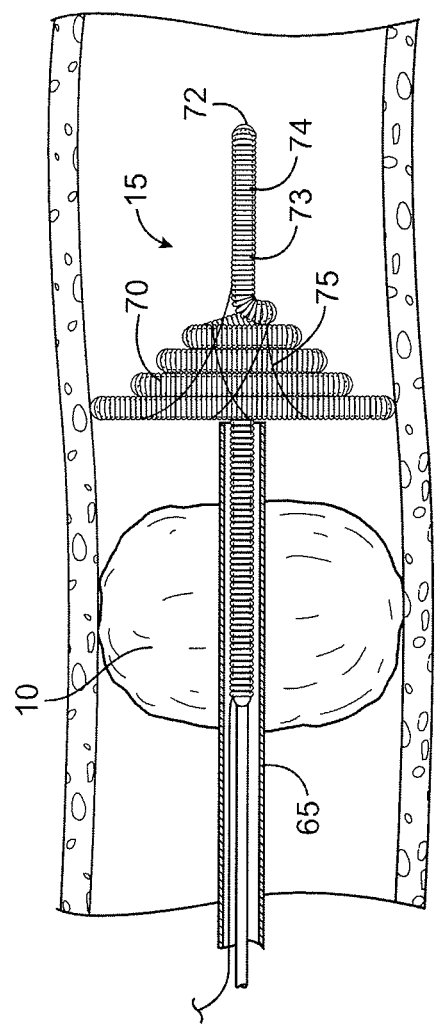
FIG. 7 shows the thrombectomy device advanced further into the vasculature to a position distal to the thrombotic occlusion.

Use of the vascular access and reverse flow system with the thrombectomy device 15 is now described. The arterial access device 110 is introduced into the common carotid artery CCA of the patient and positioned in the distal common carotid artery or internal carotid artery, as shown in FIG. 5B. The thrombectomy device 15 is then advanced through the arterial access device 110, either with or without the microcatheter 60, into the carotid artery. Before advancing the thrombectomy device 15 further, the occlusion element 129 on the arterial access device 110 may be expanded to reduce or even stop antegrade flow through the vessel. Stopping flow in the vessel may help prevent the thrombotic emboli or any parts thereof from migrating downstream due to antegrade flow during positioning of the thrombectomy device 15 or retrieval of the thrombus. The thrombectomy device 15 is then advanced, either through the microcatheter 60 or by itself within the sheath 65, further into the vasculature to a position proximal to, within or distal to the thrombotic occlusion 10, as shown in FIG. 7. During any part of the procedure, reverse flow may be initiated in the vessel via a retrograde flow system (described below) and/or via active aspiration.

Figure 8:
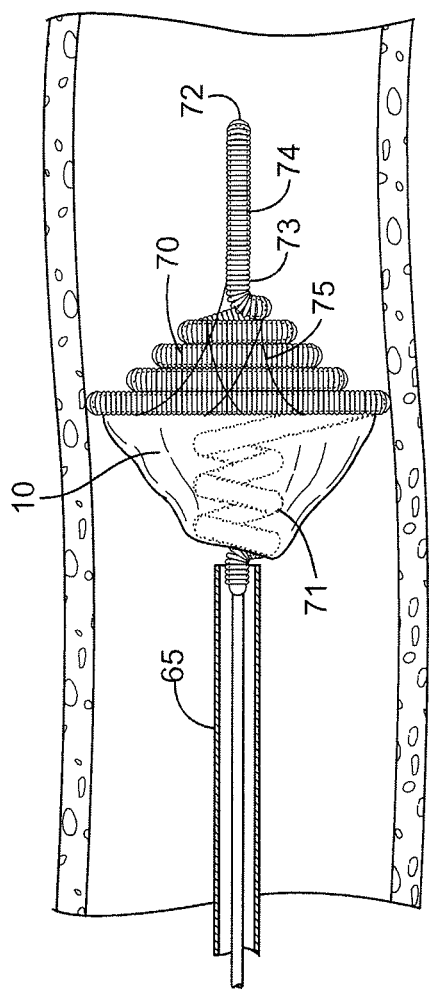
FIG. 8 shows coils of the thrombectomy device engaging the thrombotic occlusion.

The thrombectomy device 15 is then placed into the thrombotic occlusion 10 and possibly through the thrombotic occlusion. The engaging element 68 is then advanced out of the microcatheter 60 or sheath 65 to permit the distal portion 70 of the engaging element 68 to expand at a location beyond the thrombotic occlusion. In this manner, the relatively closed distal portion 70 prevents the thrombotic occlusion, or any part thereof, from migrating downstream. The proximal portion 71 is then advanced out of the sheath 65 or microcatheter 60 so that the smaller coils of the proximal portion 71 engage the thrombotic occlusion 10 as shown in FIG. 8.

Figure 9:
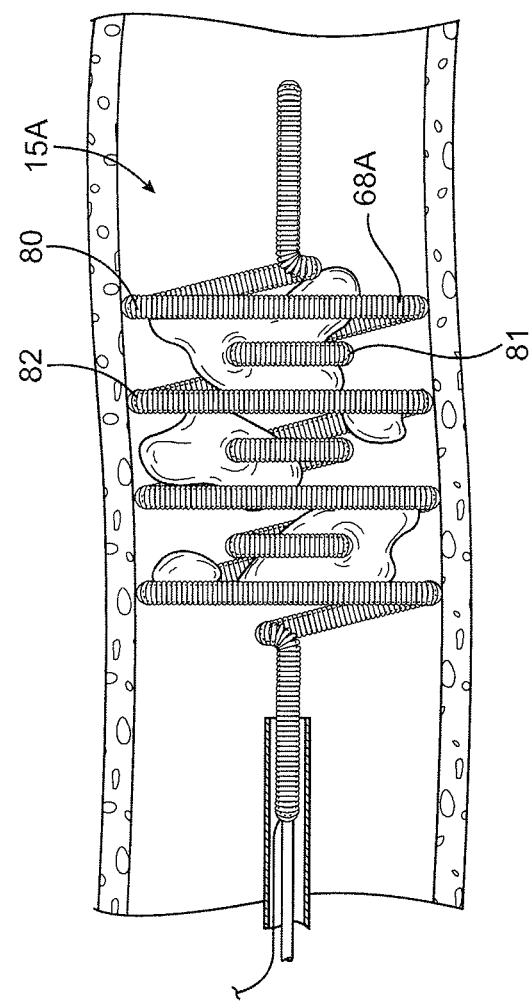
FIG. 9 shows another embodiment of a thrombectomy device.

Referring to FIG. 9, another thrombectomy device 15A is shown wherein the same or similar reference numbers refer to the same or similar structure. The thrombectomy device 15A has a first section 80 with larger diameter coils than a second section 81. A third section 82 also has larger coils than the second section 81 with the second section 81 positioned between the first and third sections. The thrombectomy device 15A may have a number of alternating small and large sections which can enhance the ability of the thrombectomy device 15A to engage various thrombotic occlusions.

The thrombectomy device 15A may be used in any suitable manner to engage the thrombotic occlusion. For example, the microcatheter 60 or sheath 65 may be advanced through the thrombotic occlusion and then retracted to expose the thrombectomy device 15A. The thrombectomy device 15A is then retracted into the thrombotic occlusion to engage the thrombotic occlusion. The thrombectomy device 15A may be rotated when moved into the thrombotic occlusion to take advantage of the generally helical shape of the obstruction removal device. The thrombectomy device 15A may also be used to engage the thrombotic occlusion by simply retracting the microcatheter 60 or sheath 65 with the thrombectomy device 15A expanding within the thrombotic occlusion. Finally, the engaging element 68A may be exposed and expanded proximal to the thrombotic occlusion and then advanced into the thrombotic occlusion.

When advancing the thrombectomy device 15A into the thrombotic occlusion, the user may also twist the thrombectomy device 15A to take advantage of the generally helical shape. The alternating large and small sections enhance the ability of the engaging element 68A to engage varying shapes and sizes of thrombotic occlusion. Another method of aiding mechanical capture of an thrombotic occlusion is to coat the device and elements of the device with a material 77 which helps to adhere the thrombotic occlusion, and in particular thrombus, to the device or element. The material may be, for example, fibrin or may be any other suitable material.

It may be appreciated that other mechanical thrombectomy catheters may be used in a similar manner with the vascular access and reverse flow system as described above. Mechanical thrombectomy devices may include variations on the thrombus retrieval device described above, such as expandable cages, wire or filament loops, graspers, brushes, or the like. These clot retrievers may include aspiration lumens to lower the risk of embolic debris leading to ischemic complications. Alternately, thrombectomy devices may include clot disruption elements such as fluid vortices, ultrasound or laser energy elements, balloons, or the like, coupled with flushing and aspiration to remove the thrombus. Some exemplary devices and methods are described in the following U.S. Patents and Patent Publications, which are all incorporated by reference in their entirety: U.S. Pat. No. 6,663,650, U.S. Pat. No. 6,730,104; U.S. Pat. No. 6,428,531, U.S. Pat. No. 6,379,325, U.S. Pat. No. 6,481,439, U.S. Pat. No. 6,929,632, U.S. Pat. No. 5,938,645, U.S. Pat. No. 6,824,545, U.S. Pat. No. 6,679,893, U.S. Pat. No. 6,685,722, U.S. Pat. No. 6,436,087, U.S. Pat. No. 5,794,629, U.S. Patent Pub. No. 20080177245, U.S. Patent Pub. No. 20090299393, U.S. Patent Pub. No. 20040133232, U.S. Patent Pub. No. 20020183783, U.S. Patent Pub. No. 20070198028, U.S. Patent Pub. No. 20060058836, U.S. Patent Pub. No. 20060058837, U.S. Patent Pub. No. 20060058838, U.S. Patent Pub. No. 20060058838, U.S. Patent Pub. No. 20030212384, and U.S. Patent Pub. No. 20020133111.

EXEMPLARY EMBODIMENTS OF PERFUSION CATHETER

Figure 25:
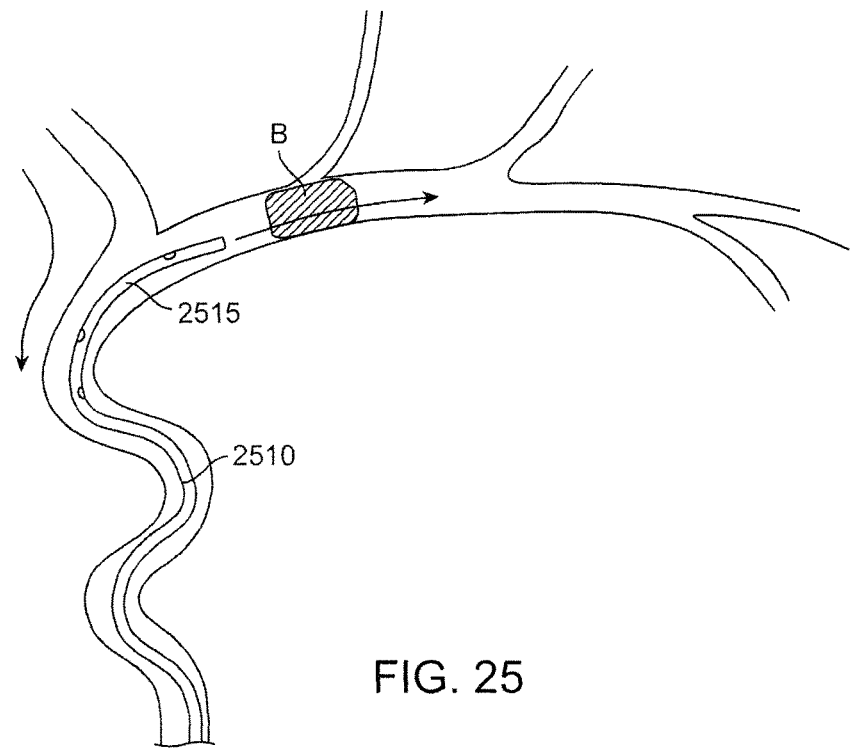
FIG. 25 shows a perfusion catheter positioned adjacent to a thrombotic blockage in the vasculature.
Figure 26:
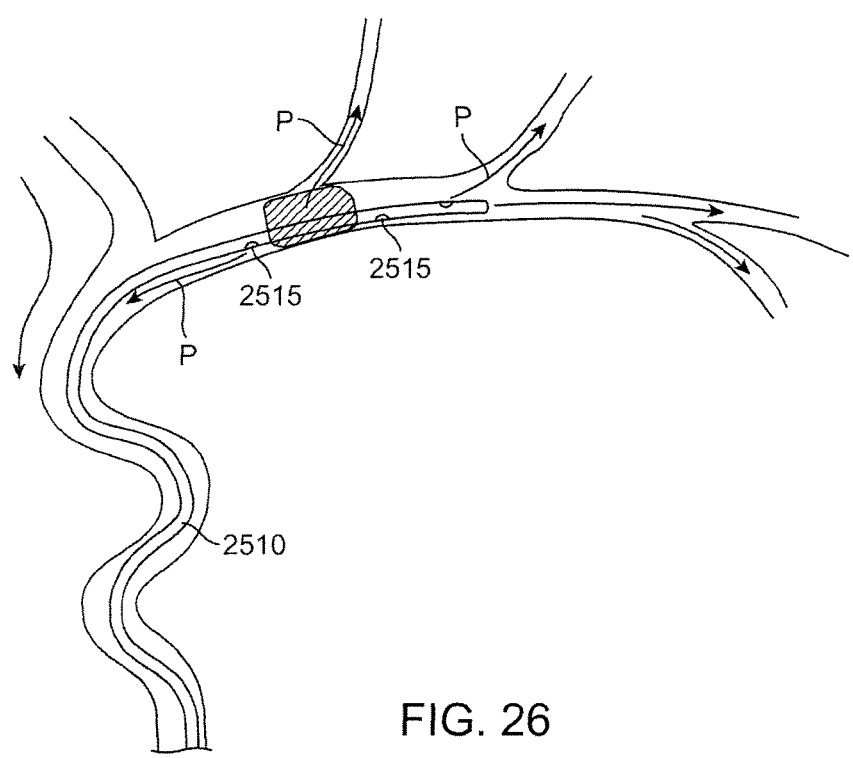
FIG. 26 shows the perfusion catheter positioned across the thrombotic blockage to enable perfusion distal to the blockage.

Some exemplary embodiments of perfusion catheters are now described. FIG. 25 shows a perfusion catheter 2510 positioned adjacent to a thrombotic blockage B in the vasculature. FIG. 26 shows the perfusion catheter 2510 positioned across the thrombotic blockage B, to enable perfusion distal to the blockage. In an embodiment, the catheter is 2510 positioned over a guidewire placed through a lumen in the catheter. The lumen may serve as both a guidewire lumen and a perfusion lumen. Once placed, the guidewire may be removed to maximize the throughspace of the lumen available for perfusion. Alternately, the guidewire lumen and the perfusion lumen may be two separate lumens within the catheter, so that the guidewire may remain in place in the guidewire lumen during perfusion without interfering with the perfusion lumen. Perfusion exit holes 2515, which communicate with the perfusion lumen, are located in a distal region of the catheter 2510. The perfusion exit holes 2515 may be used to perfuse the vasculature distal to the blockage B, as exhibited by the arrows P in FIG. 26, which represent the flow of perfusion solution out of the catheter 2510. Alternately, the catheter 2510 may be positioned relative to the blockage B such that the perfusion exit holes 2515 are initially positioned just proximal to, or within, the thrombotic blockage B during a bolus of thrombolytic infusion. The catheter can then be re-positioned so that at least some of the perfusion exit holes 2515 are located distal of the blockage B to provide distal perfusion with blood or an equivalent solution to the ischemic penumbra.

Figure 27A:
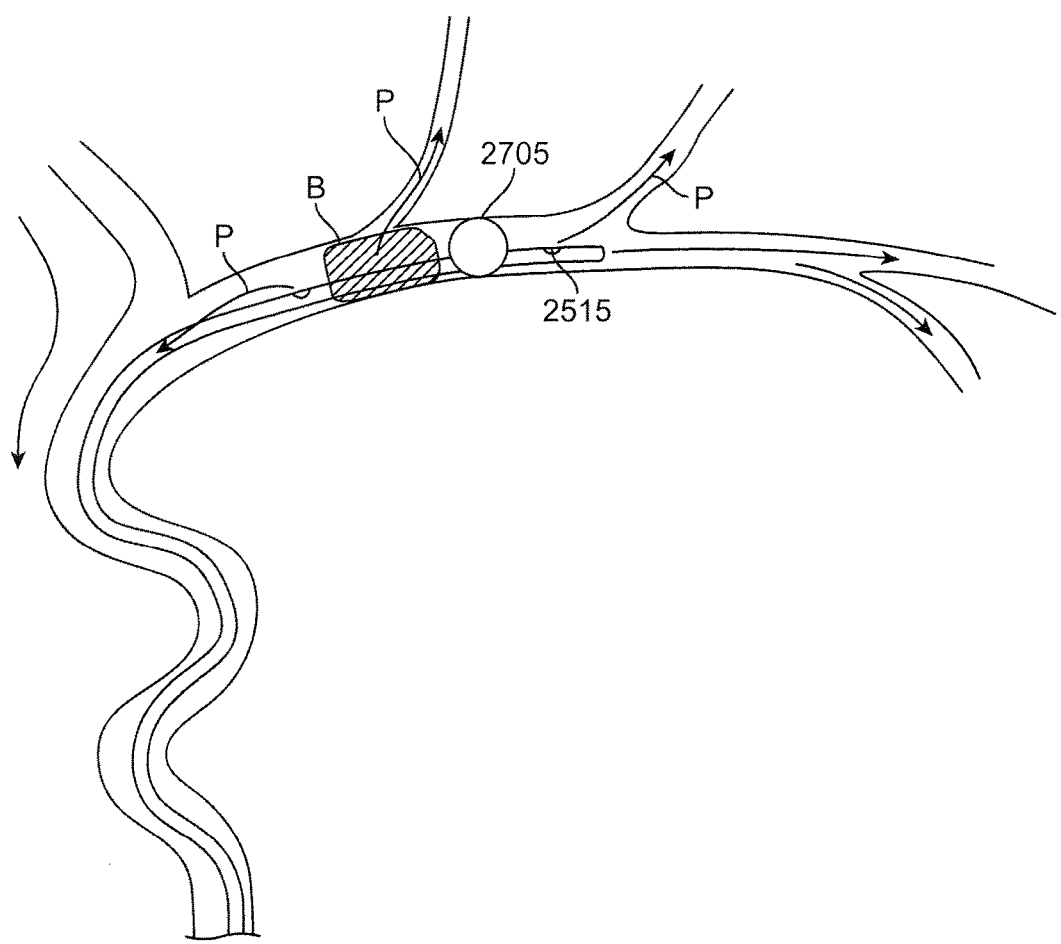
FIG. 27A shows a perfusion catheter that includes an occlusion balloon with perfusion holes.

In a variation to this embodiment, shown in FIG. 27A, the perfusion catheter 2510 may include an occlusion balloon 2705, with perfusion exit holes 2515 positioned distal to, and/or proximal to the occlusion balloon 2705. As with the previous embodiment, the perfusion catheter 2510 may be used in conjunction with recanalization therapies such as thrombectomy devices or intra-arterial thrombolytic infusion. The catheter 2510 is placed in the vasculature so that the occlusion balloon 2705 is positioned distal to the blockage B. The catheter 2510 may be configured to perfuse the region distal of the balloon 2705 with blood or equivalent, and the region proximal of the balloon 2705 with thrombolytic agents. In this regard, the catheter 2510 may include separate perfusion lumens 2720a and 2720b that communicate with separate perfusion exit holes, as shown in FIG. 27B. Alternately, the distal and proximal perfusion exit holes are connected to the same perfusion lumen 2720, and regions both distal and proximal to the occlusion balloon are used to infuse blood or equivalent, as shown in FIG. 27C. The proximal perfusion provides a pressure gradient just proximal to the blockage, and causes any embolic debris generated during recanalization of the occlusion 10 into the reverse flow path at the terminal internal carotid artery ICA, as shown in FIG. 27A. In addition, the proximal perfusion can supply blood to smaller vessels (perforators) originating in or just proximal to the occlusion.

It should be appreciated that other perfusion catheters may be used with the system 100, for example those described by U.S. Pat. Nos. 6,435,189 and 6,295,990, which are incorporated by reference in their entirety.

EXEMPLARY EMBODIMENT OF RETROGRADE BLOOD FLOW SYSTEM

As discussed, the system 100 includes the arterial access device 110, venous return device 115, and shunt 120 which provides a passageway for retrograde flow from the arterial access device 110 to the venous return device 115. The system also includes the flow control assembly 125, which interacts with the shunt 120 to regulate and/or monitor retrograde blood flow through the shunt 120. Exemplary embodiments of the components of the system 100 are now described.

Arterial Access Device

FIG. 10A shows an exemplary embodiment of the arterial access device 110, which comprises a distal sheath 605, a proximal extension 610, a flow line 615, an adaptor or Y-connector 620, and a hemostasis valve 625. The distal sheath 605 is adapted to be introduced through an incision or puncture in a wall of a common carotid artery, either an open surgical incision or a percutaneous puncture established, for example, using the Seldinger technique. The length of the sheath can be in the range from 5 to 15 cm, usually being from 10 cm to 12 cm. The inner diameter is typically in the range from 7 Fr (1 Fr=0.33 mm), to 10 Fr, usually being 8 Fr. Particularly when the sheath is being introduced through the transcervical approach, above the clavicle but below the carotid bifurcation, it is desirable that the sheath 605 be highly flexible while retaining hoop strength to resist kinking and buckling. Thus, the distal sheath 605 can be circumferentially reinforced, such as by braid, helical ribbon, helical wire, or the like. In an alternate embodiment, the distal sheath is adapted to be introduced through a percutaneous puncture into the femoral artery, such as in the groin, and up the aortic arch into the target common carotid artery CCA.

The distal sheath 605 can have a stepped or other configuration having a reduced diameter distal region 630, as shown in FIG. 10B, which shows an enlarged view of the distal region 630 of the sheath 605. The distal region 630 of the sheath can be sized for insertion into the carotid artery, typically having an inner diameter in the range from 2.16 mm (0.085 inch) to 2.92 mm (0.115 inch) with the remaining proximal region of the sheath having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm or 3 cm to 5 cm. In another embodiment, the length of the reduced-diameter distal section 630 has a length of approximately 10 cm to 15 cm. The relatively short length of the reduced-diameter distal section 630 permits this section to be positioned in the common carotid artery CCA via the transcervical approach with reduced risk that the distal end of the sheath 605 will contact the bifurcation B. Moreover, the reduced diameter section 630 also permits a reduction in size of the arteriotomy for introducing the sheath 605 into the artery while having a minimal impact in the level of flow resistance.

With reference again to FIG. 10A, the proximal extension 610 has an inner lumen which is contiguous with an inner lumen of the sheath 605. The lumens can be joined by the Y-connector 620 which also connects a lumen of the flow line 615 to the sheath. In the assembled system, the flow line 615 connects to and forms a first leg of the retrograde shunt 120 (FIG. 5A). The proximal extension 610 can have a length sufficient to space the hemostasis valve 625 well away from the Y-connector 620, which is adjacent to the percutaneous or surgical insertion site. By spacing the hemostasis valve 625 away from a percutaneous insertion site, the physician can introduce a stent delivery system or other working catheter into the proximal extension 610 and sheath 605 while staying out of the fluoroscopic field when fluoroscopy is being performed.

A flush line 635 can be connected to the side of the hemostasis valve 625 and can have a stopcock 640 at its proximal or remote end. The flush-line 635 allows for the introduction of saline, contrast fluid, or the like, during the procedures. The flush line 635 can also allow pressure monitoring during the procedure. A dilator 645 having a tapered distal end 650 can be provided to facilitate introduction of the distal sheath 605 into the common carotid artery. The dilator 645 can be introduced through the hemostasis valve 625 so that the tapered distal end 650 extends through the distal end of the sheath 605, as best seen in FIG. 11A. The dilator 645 can have a central lumen to accommodate a guide wire. Typically, the guide wire is placed first into the vessel, and the dilator/sheath combination travels over the guide wire as it is being introduced into the vessel.

Optionally, a tube 705 may be provided which is coaxially received over the exterior of the distal sheath 605, also as seen in FIG. 11A. The tube 705 has a flared proximal end 710 which engages the adapter 620 and a distal end 715. Optionally, the distal end 715 may be beveled, as shown in FIG. 11B. The tube 705 may serve at least two purposes. First, the length of the tube 705 limits the introduction of the sheath 605 to the exposed distal portion of the sheath 605, as seen in FIG. 11A. Second, the tube 705 can engage a pre-deployed puncture closure device disposed in the carotid artery wall, if present, to permit the sheath 605 to be withdrawn without dislodging the closure device.

The distal sheath 605 can be configured to establish a curved transition from a generally anterior-posterior approach over the common carotid artery to a generally axial luminal direction within the common carotid artery. The transition in direction is particularly useful when a percutaneous access is provided through the common carotid wall. While an open surgical access may allow for some distance in which to angle a straight sheath into the lumen of the common carotid artery, percutaneous access will generally be in a normal or perpendicular direction relative to the access of the lumen, and in such cases, a sheath that can flex or turn at an angle will find great use.

The sheath 605 can be formed in a variety of ways. For example, the sheath 605 can be pre-shaped to have a curve or an angle some set distance from the tip, typically 2 to 3 cm. The pre-shaped curve or angle can typically provide for a turn in the range from 20° to 90°, preferably from 30° to 70°. For initial introduction, the sheath 605 can be straightened with an obturator or other straight or shaped instrument such as the dilator 645 placed into its lumen. After the sheath 605 has been at least partially introduced through the percutaneous or other arterial wall penetration, the obturator can be withdrawn to allow the sheath 605 to reassume its pre-shaped configuration into the arterial lumen.

Other sheath configurations include having a deflection mechanism such that the sheath can be placed and the catheter can be deflected in situ to the desired deployment angle. In still other configurations, the catheter has a non-rigid configuration when placed into the lumen of the common carotid artery. Once in place, a pull wire or other stiffening mechanism can be deployed in order to shape and stiffen the sheath into its desired configuration. One particular example of such a mechanism is commonly known as "shape-lock" mechanisms as well described in medical and patent literature.

Another sheath configuration comprises a curved dilator inserted into a straight but flexible sheath, so that the dilator and sheath are curved during insertion. The sheath is flexible enough to conform to the anatomy after dilator removal.

In an embodiment, the sheath has built-in puncturing capability and atraumatic tip analogous to a guide wire tip. This eliminates the need for needle and wire exchange currently used for arterial access according to the micro-puncture technique, and can thus save time, reduce blood loss, and require less surgeon skill.

FIG. 12A shows another embodiment of the arterial access device 110. This embodiment is substantially the same as the embodiment shown in FIG. 10A, except that the distal sheath 605 includes an occlusion element 129 for occluding flow through, for example the common carotid artery. If the occluding element 129 is an inflatable structure such as a balloon or the like, the sheath 605 can include an inflation lumen that communicates with the occlusion element 129. The occlusion element 129 can be an inflatable balloon, but it could also be an inflatable cuff, a conical or other circumferential element which flares outwardly to engage the interior wall of the common or internal carotid artery to block flow therepast, a membrane-covered braid, a slotted tube that radially enlarges when axially compressed, or similar structure which can be deployed by mechanical means, or the like. In the case of balloon occlusion, the balloon can be compliant, non-compliant, elastomeric, reinforced, or have a variety of other characteristics. In an embodiment, the balloon is an elastomeric balloon which is closely received over the exterior of the distal end of the sheath prior to inflation. When inflated, the elastomeric balloon can expand and conform to the inner wall of the common carotid artery. In an embodiment, the elastomeric balloon is able to expand to a diameter at least twice that of the non-deployed configuration, frequently being able to be deployed to a diameter at least three times that of the undeployed configuration, more preferably being at least four times that of the undeployed configuration, or larger.

Figure 28:
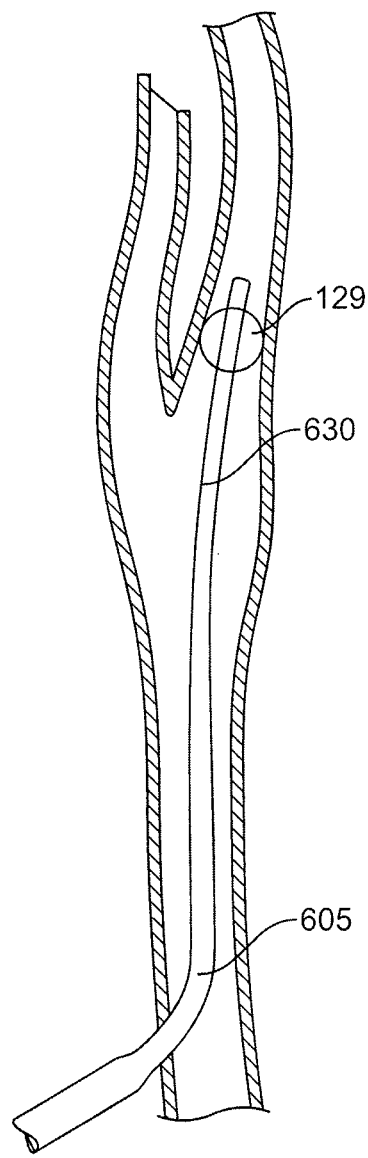
FIG. 28 shows an arterial access device having a stepped configuration, with an occlusion element.

As shown in FIG. 12B, the distal sheath 605 with the occlusion element 129 can have a stepped or other configuration having a reduced diameter distal region 630. The distal region 630 can be sized for insertion into the carotid artery with the remaining proximal region of the sheath 605 having larger outside and luminal diameters, with the inner diameter typically being in the range from 2.794 mm (0.110 inch) to 3.43 mm (0.135 inch). The larger luminal diameter of the proximal region minimizes the overall flow resistance of the sheath. In an embodiment, the reduced-diameter distal section 630 has a length of approximately 2 cm to 4 cm or 3 cm to 5 cm. In another embodiment, the length of the reduced-diameter distal section 630 has a length of approximately 10 cm to 15 cm. The relatively short length of the reduced-diameter distal section 630 permits this section to be positioned in the common carotid artery CCA via the transcervical approach with reduced risk that the distal end of the sheath 605 will contact the bifurcation B. In an alternate embodiment, shown in FIG. 28, the reduced diameter distal section 630 is tapered or stepped and has a length of approximately 10 cm to 15 cm, such that the distal tip can be positioned in the internal carotid artery ICA.

Figure 29:
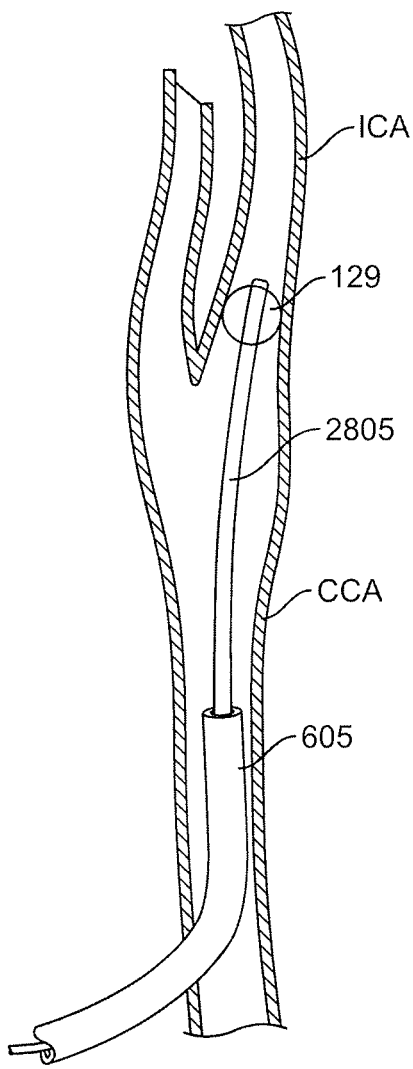
FIG. 29 shows an arterial access device, and an additional sub-selective sheath with occlusion element placed through the arterial access device and occluding a distal artery
Figure 30:
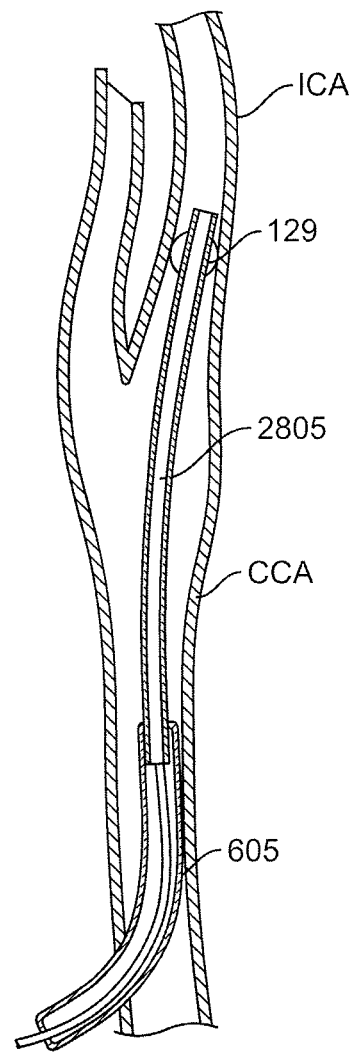
FIG. 30 shows the arterial access device, and a telescoping extension with an occlusion element which extends the lumen of the arterial access device into a distal artery and occludes the distal artery.

In another embodiment, shown in FIG. 29, the arterial access device 110 is introduced into an incision in the common carotid artery CCA via a transcervical approach, and is used to introduce a separate sub-selective sheath 2805 into the internal carotid artery ICA. The sub-selective sheath 2805 can be smaller in diameter and more flexible than the access sheath 605 of the arterial access device 110, to allow catheterization of the more distal and potentially more tortuous vessel. The sub-selective sheath 2805 may be co-axial with the access sheath 605, with a reduced diameter that allows introduction through the access sheath 605. Alternately, as shown in FIG. 30, the sub-selective sheath 2805 may be constructed in a telescoping manner with the access sheath 605 to extend the lumen of the access sheath 605. In this configuration, the sub-selective sheath 2805 takes up minimal luminal area in the access sheath 605, thus optimizing the reverse flow rate. In either configuration, the occlusion element 129 is located on the distal end of the subselective sheath 2805 rather than on the access sheath 605.

Venous Return Device

Figure 13:
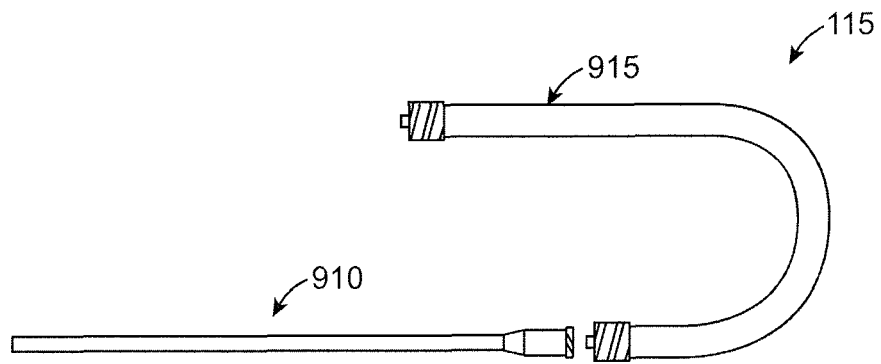
FIG. 13 illustrates a first embodiment of a venous return device useful in the methods and systems of the present disclosure.
Figure 14:
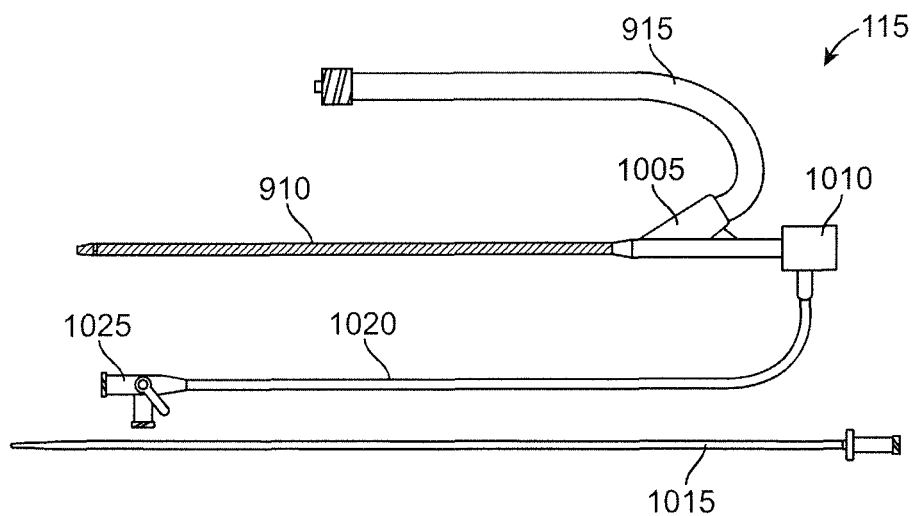
FIG. 14 illustrates an alternative venous return device useful in the methods and systems of the present disclosure.

Referring now to FIG. 13, the venous return device 115 can comprise a distal sheath 910 and a flow line 915, which connects to and forms a leg of the shunt 120 when the system is in use. The distal sheath 910 is adapted to be introduced through an incision or puncture into a venous return location, such as the jugular vein or femoral vein. The distal sheath 910 and flow line 915 can be permanently affixed, or can be attached using a conventional luer fitting, as shown in FIG. 13. Optionally, as shown in FIG. 14, the sheath 910 can be joined to the flow line 915 by a Y-connector 1005. The Y-connector 1005 can include a hemostasis valve 1010, permitting insertion of a dilator 1015 to facilitate introduction of the venous return device into the internal jugular vein or other vein. As with the arterial access dilator 645, the venous dilator 1015 includes a central guide wire lumen so the venous sheath and dilator combination can be placed over a guide wire. Optionally, the venous sheath 910 can include a flush line 1020 with a stopcock 1025 at its proximal or remote end.

In order to reduce the overall system flow resistance, the arterial access flow line 615 and Y-connector 620 (FIG. 10A) and the venous return flow line 915, and Y-connectors 1005 (FIG. 13 or 14), can each have a relatively large flow lumen inner diameter, typically being in the range from 2.54 mm (0.100 inch) to 5.08 mm (0.200 inch), and a relatively short length, typically being in the range from 10 cm to 20 cm. The low system flow resistance is desirable since it permits the flow to be maximized during portions of a procedure when the risk of emboli is at its greatest. The low system flow resistance also allows the use of a variable flow resistance for controlling flow in the system, as described in more detail below. The dimensions of the venous return sheath 910 can be generally the same as those described for the arterial access sheath 605 above. In the venous return sheath, an extension for the hemostasis valve 1010 is not required.

Retrograde Shunt

The shunt 120 can be formed of a single tube or multiple, connected tubes that provide fluid communication between the arterial access catheter 110 and the venous return catheter 115 to provide a pathway for retrograde blood flow therebetween. As shown in FIG. 5A, the shunt 120 connects at one end to the flow line 615 of the arterial access device 110, and at an opposite end to the flow line 915 of the venous return catheter 115.

In an embodiment, the shunt 120 can be formed of at least one tube that communicates with the flow control assembly 125. The shunt 120 can be any structure that provides a fluid pathway for blood flow. The shunt 120 can have a single lumen or it can have multiple lumens. The shunt 120 can be removably attached to the flow control assembly 125, arterial access device 110, and/or venous return device 115. Prior to use, the user can select a shunt 120 with a length that is most appropriate for use with the arterial access location and venous return location. In an embodiment, the shunt 120 can include one or more extension tubes that can be used to vary the length of the shunt 120. The extension tubes can be modularly attached to the shunt 120 to achieve a desired length. The modular aspect of the shunt 120 permits the user to lengthen the shunt 120 as needed depending on the site of venous return. For example, in some patients, the internal jugular vein IJV is small and/or tortuous. The risk of complications at this site may be higher than at some other locations, due to proximity to other anatomic structures. In addition, hematoma in the neck may lead to airway obstruction and/or cerebral vascular complications. Consequently, for such patients it may be desirable to locate the venous return site at a location other than the internal jugular vein IJV, such as the femoral vein. A femoral vein return site may be accomplished percutaneously, with lower risk of serious complication, and also offers an alternative venous access to the central vein if the internal jugular vein IJV is not available. Furthermore, the femoral venous return changes the layout of the reverse flow shunt such that the shunt controls may be located closer to the "working area" of the intervention, where the devices are being introduced and the contrast injection port is located.

In an embodiment, the shunt 120 has an internal diameter of 4.76 mm (3/16 inch) and has a length of 40-70 cm. As mentioned, the length of the shunt can be adjusted.

In an embodiment, the shunt may contain a port which can be connected to an aspiration source such as a syringe, suction pump, or the like.

In an additional embodiment, the shunt may contain an element that connects to an active pump, for example a peristaltic pump, a diaphragm pump, an impeller pump, or a syringe pump.

Flow Control Assembly—Regulation and Monitoring of Retrograde Flow

The flow control assembly 125 interacts with the retrograde shunt 120 to regulate and/or monitor the retrograde flow rate from the common carotid artery to the venous return site, such as the internal jugular vein, or to the external receptacle. In this regard, the flow control assembly 125 enables the user to achieve higher maximum flow rates than existing systems and to also selectively adjust, set, or otherwise modulate the retrograde flow rate. Various mechanisms can be used to regulate the retrograde flow rate, as described more fully below. The flow control assembly 125 enables the user to configure retrograde blood flow in a manner that is suited for various treatment regimens, as described below.

In general, the ability to control the continuous retrograde flow rate allows the physician to adjust the protocol for individual patients and stages of the procedure. The retrograde blood flow rate will typically be controlled over a range from a low rate to a high rate. The high rate can be at least two fold higher than the low rate, typically being at least three fold higher than the low rate, and often being at least five fold higher than the low rate, or even higher. In an embodiment, the high rate is at least three fold higher than the low rate and in another embodiment the high rate is at least six fold higher than the low rate. While it is generally desirable to have a high retrograde blood flow rate to maximize the extraction of emboli from the carotid arteries, the ability of patients to tolerate retrograde blood flow will vary. Thus, by having a system and protocol which allows the retrograde blood flow rate to be easily modulated, the treating physician can determine when the flow rate exceeds the tolerable level for that patient and set the reverse flow rate accordingly. For patients who cannot tolerate continuous high reverse flow rates, the physician can chose to turn on high flow only for brief, critical portions of the procedure when the risk of embolic debris is highest. At short intervals, for example between 15 seconds and 1 minute, patient tolerance limitations are usually not a factor.

In specific embodiments, the continuous retrograde blood flow rate can be controlled at a base line flow rate in the range from 10 ml/min to 200 ml/min, typically from 20 ml/min to 100 ml/min. These flow rates will be tolerable to the majority of patients. Although flow rate is maintained at the base line flow rate during most of the procedure, at times when the risk of emboli release is increased, the flow rate can be increased above the base line for a short duration in order to improve the ability to capture such emboli. For example, the retrograde blood flow rate can be increased above the base line when the stent catheter is being introduced, when the stent is being deployed, pre- and post-dilatation of the stent, removal of the common carotid artery occlusion, and the like.

The flow rate control system can be cycled between a relatively low flow rate and a relatively high flow rate in order to "flush" the carotid arteries in the region of the carotid bifurcation prior to reestablishing antegrade flow. Such cycling can be established with a high flow rate which can be approximately two to six fold greater than the low flow rate, typically being about three fold greater. The cycles can typically have a length in the range from 0.5 seconds to 10 seconds, usually from 2 seconds to 5 seconds, with the total duration of the cycling being in the range from 5 seconds to 60 seconds, usually from 10 seconds to 30 seconds.

Figure 15:
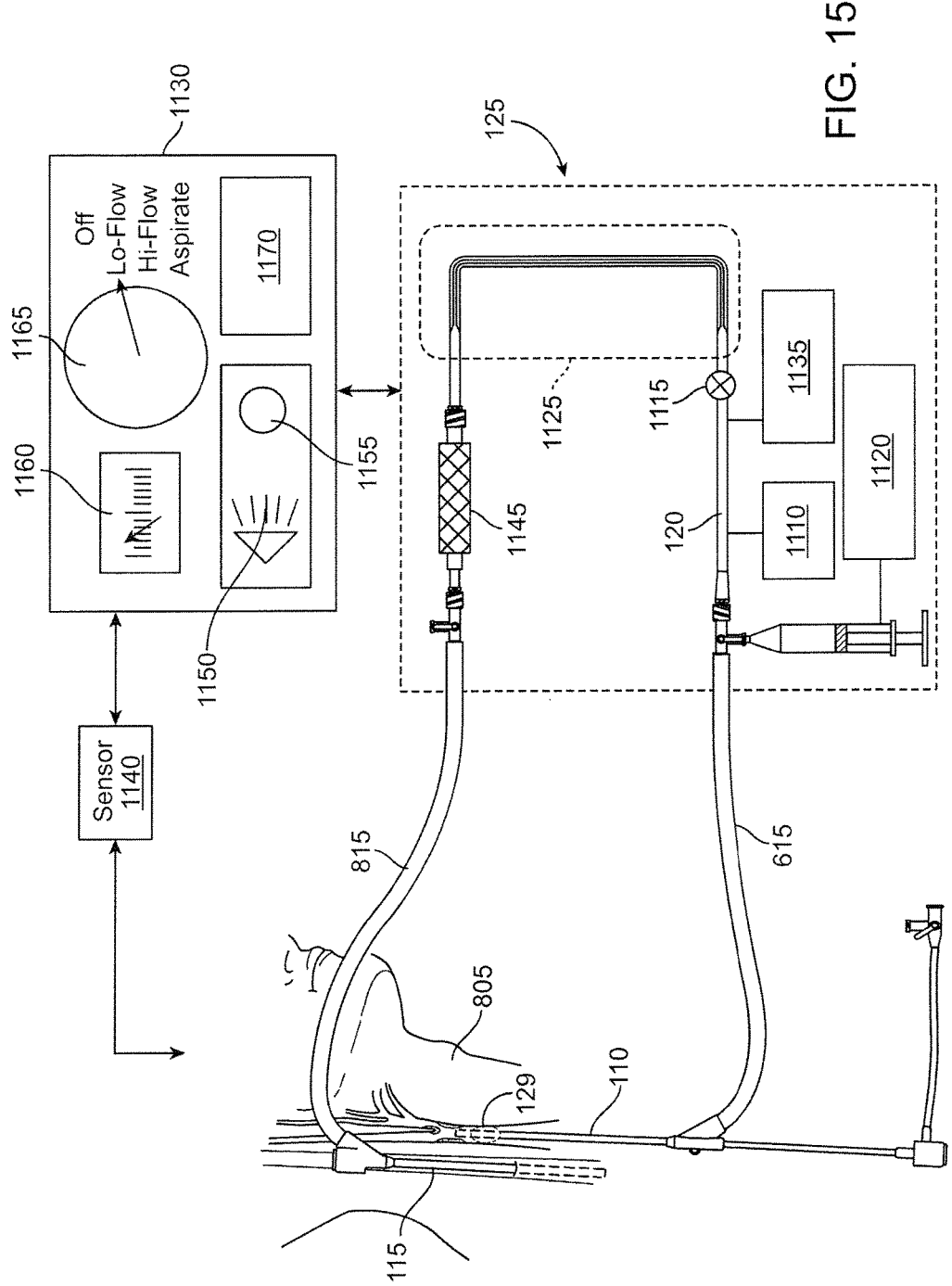
FIG. 15 shows an example of the reverse flow system with a schematic representation of the flow control assembly.

FIG. 15 shows an example of the system 100 with a schematic representation of the flow control assembly 125, which is positioned along the shunt 120 such that retrograde blood flow passes through or otherwise communicates with at least a portion of the flow control assembly 125. The flow control assembly 125 can include various controllable mechanisms for regulating and/or monitoring retrograde flow. The mechanisms can include various means of controlling the retrograde flow, including one or more pumps 1110, valves 1115, syringes 1120 and/or a variable resistance component 1125. The flow control assembly 125 can be manually controlled by a user and/or automatically controlled via a controller 1130 to vary the flow through the shunt 120. For example, varying the flow resistance, the rate of retrograde blood flow through the shunt 120 can be controlled. The controller 1130, which is described in more detail below, can be integrated into the flow control assembly 125 or it can be a separate component that communicates with the components of the flow control assembly 125.

In addition, the flow control assembly 125 can include one or more flow sensors 1135 and/or anatomical data sensors 1140 (described in detail below) for sensing one or more aspects of the retrograde flow. A filter 1145 can be positioned along the shunt 120 for removing emboli before the blood is returned to the venous return site. When the filter 1145 is positioned upstream of the controller 1130, the filter 1145 can prevent emboli from entering the controller 1145 and potentially clogging the variable flow resistance component 1125. It should be appreciated that the various components of the flow control assembly 125 (including the pump 1110, valves 1115, syringes 1120, variable resistance component 1125, sensors 1135/1140, and filter 1145) can be positioned at various locations along the shunt 120 and at various upstream or downstream locations relative to one another. The components of the flow control assembly 125 are not limited to the locations shown in FIG. 15. Moreover, the flow control assembly 125 does not necessarily include all of the components but can rather include various sub-combinations of the components. For example, a syringe could optionally be used within the flow control assembly 125 for purposes of regulating flow or it could be used outside of the assembly for purposes other than flow regulation, such as to introduce fluid such as radiopaque contrast into the artery in an antegrade direction via the shunt 120.

Both the variable resistance component 1125 and the pump 1110 can be coupled to the shunt 120 to control the retrograde flow rate. The variable resistance component 1125 controls the flow resistance, while the pump 1110 provides for positive displacement of the blood through the shunt 120. Thus, the pump can be activated to drive the retrograde flow rather than relying on the perfusion stump pressures of the ECA and ICA and the venous back pressure to drive the retrograde flow. The pump 1110 can be a peristaltic tube pump or any type of pump including a positive displacement pump. The pump 1110 can be activated and deactivated (either manually or automatically via the controller 1130) to selectively achieve blood displacement through the shunt 120 and to control the flow rate through the shunt 120. Displacement of the blood through the shunt 120 can also be achieved in other manners including using the aspiration syringe 1120, or a suction source such as a vacutainer, vaculock syringe, or wall suction may be used. The pump 1110 can communicate with the controller 1130.

One or more flow control valves 1115 can be positioned along the pathway of the shunt. The valve(s) can be manually actuated or automatically actuated (via the controller 1130). The flow control valves 1115 can be, for example one-way valves to prevent flow in the antegrade direction in the shunt 120, check valves, or high pressure valves which would close off the shunt 120, for example during high-pressure contrast injections (which are intended to enter the arterial vasculature in an antegrade direction).

The controller 1130 communicates with components of the system 100 including the flow control assembly 125 to enable manual and/or automatic regulation and/or monitoring of the retrograde flow through the components of the system 100 (including, for example, the shunt 120, the arterial access device 110, the venous return device 115 and the flow control assembly 125). For example, a user can actuate one or more actuators on the controller 1130 to manually control the components of the flow control assembly 125. Manual controls can include switches or dials or similar components located directly on the controller 1130 or components located remote from the controller 1130 such as a foot pedal or similar device. The controller 1130 can also automatically control the components of the system 100 without requiring input from the user. In an embodiment, the user can program software in the controller 1130 to enable such automatic control. The controller 1130 can control actuation of the mechanical portions of the flow control assembly 125. The controller 1130 can include circuitry or programming that interprets signals generated by sensors 1135/1140 such that the controller 1130 can control actuation of the flow control assembly 125 in response to such signals generated by the sensors.

The flow control assembly 125 may also include an active pump actuator which interfaces with an element in the shunt to enable active retrograde pumping of blood, such as a pump head for a roller pump, a rotary motor for an impeller-style pump, or the like. The controller 1130 would provide controls for the pump rate.

The representation of the controller 1130 in FIG. 15 is merely exemplary. It should be appreciated that the controller 1130 can vary in appearance and structure. The controller 1130 is shown in FIG. 15 as being integrated in a single housing. This permits the user to control the flow control assembly 125 from a single location. It should be appreciated that any of the components of the controller 1130 can be separated into separate housings. Further, FIG. 15 shows the controller 1130 and flow control assembly 125 as separate housings. It should be appreciated that the controller 1130 and flow control regulator 125 can be integrated into a single housing or can be divided into multiple housings or components.

Flow State Indicator(s)

The controller 1130 can include one or more indicators that provides a visual and/or audio signal to the user regarding the state of the retrograde flow. An audio indication advantageously reminds the user of a flow state without requiring the user to visually check the flow controller 1130. The indicator(s) can include a speaker 1150 and/or a light 1155 or any other means for communicating the state of retrograde flow to the user. The controller 1130 can communicate with one or more sensors of the system to control activation of the indicator. Or, activation of the indicator can be tied directly to the user actuating one of the flow control actuators 1165. The indicator need not be a speaker or a light. The indicator could simply be a button or switch that visually indicates the state of the retrograde flow. For example, the button being in a certain state (such as a pressed or down state) may be a visual indication that the retrograde flow is in a high state. Or, a switch or dial pointing toward a particular labeled flow state may be a visual indication that the retrograde flow is in the labeled state.

The indicator can provide a signal indicative of one or more states of the retrograde flow. In an embodiment, the indicator identifies only two discrete states: a state of "high" flow rate and a state of "low" flow rate. In another embodiment, the indicator identifies more than two flow rates, including a "high" flow rate, a "medium" flow rate, and a "low" rate. The indicator can be configured to identify any quantity of discrete states of the retrograde flow or it can identify a graduated signal that corresponds to the state of the retrograde flow. In this regard, the indicator can be a digital or analog meter 1160 that indicates a value of the retrograde flow rate, such as in ml/min or any other units.

In an embodiment, the indicator is configured to indicate to the user whether the retrograde flow rate is in a state of "high" flow rate or a "low" flow rate. For example, the indicator may illuminate in a first manner (e.g., level of brightness) and/or emit a first audio signal when the flow rate is high and then change to a second manner of illumination and/or emit a second audio signal when the flow rate is low. Or, the indicator may illuminate and/or emit an audio signal only when the flow rate is high, or only when the flow rate is low. Given that some patients may be intolerant of a high flow rate or intolerant of a high flow rate beyond an extended period of time, it can be desirable that the indicator provide notification to the user when the flow rate is in the high state. This would serve as a fail safe feature.

In another embodiment, the indicator provides a signal (audio and/or visual) when the flow rate changes state, such as when the flow rate changes from high to low and/or vice-versa. In another embodiment, the indicator provides a signal when no retrograde flow is present, such as when the shunt 120 is blocked or one of the stopcocks in the shunt 120 is closed.

Flow Rate Actuators

The controller 1130 can include one or more actuators that the user can press, switch, manipulate, or otherwise actuate to regulate the retrograde flow rate and/or to monitor the flow rate. For example, the controller 1130 can include a flow control actuator 1165 (such as one or more buttons, knobs, dials, switches, etc.) that the user can actuate to cause the controller to selectively vary an aspect of the reverse flow. For example, in the illustrated embodiment, the flow control actuator 1165 is a knob that can be turned to various discrete positions each of which corresponds to the controller 1130 causing the system 100 to achieve a particular retrograde flow state. The states include, for example, (a) OFF; (b) LO-FLOW; (c) HI-FLOW; and (d) ASPIRATE. It should be appreciated that the foregoing states are merely exemplary and that different states or combinations of states can be used. The controller 1130 achieves the various retrograde flow states by interacting with one or more components of the system, including the sensor(s), valve(s), variable resistance component, and/or pump(s). It should be appreciated that the controller 1130 can also include circuitry and software that regulates the retrograde flow rate and/or monitors the flow rate such that the user wouldn't need to actively actuate the controller 1130.

The OFF state corresponds to a state where there is no retrograde blood flow through the shunt 120. When the user sets the flow control actuator 1165 to OFF, the controller 1130 causes the retrograde flow to cease, such as by shutting off valves or closing a stop cock in the shunt 120. The LO-FLOW and HI-FLOW states correspond to a low retrograde flow rate and a high retrograde flow rate, respectively. When the user sets the flow control actuator 1165 to LO-FLOW or HI-FLOW, the controller 1130 interacts with components of the flow control regulator 125 including pump(s) 1110, valve(s) 1115 and/or variable resistance component 1125 to increase or decrease the flow rate accordingly. Finally, the ASPIRATE state corresponds to opening the circuit to a suction source, for example a vacutainer or suction unit, if active retrograde flow is desired. The suction source can be coupled to any portion of the circuit, including the shunt 120 or the arterial access device 110.

The system can be used to vary the blood flow between various states including an active state, a passive state, an aspiration state, and an off state. The active state corresponds to the system using a means that actively drives retrograde blood flow. Such active means can include, for example, a pump, syringe, vacuum source, etc. The passive state corresponds to when retrograde blood flow is driven by the perfusion stump pressures of the ECA and ICA and possibly the venous pressure. The aspiration state corresponds to the system using a suction source, for example a vacutainer or suction unit, to drive retrograde blood flow. The off state corresponds to the system having zero retrograde blood flow such as the result of closing a stopcock or valve. The low and high flow rates can be either passive or active flow states. In an embodiment, the particular value (such as in ml/min) of either the low flow rate and/or the high flow rate can be predetermined and/or pre-programmed into the controller such that the user does not actually set or input the value. Rather, the user simply selects "high flow" and/or "low flow" (such as by pressing an actuator such as a button on the controller 1130) and the controller 1130 interacts with one or more of the components of the flow control assembly 125 to cause the flow rate to achieve the predetermined high or low flow rate value. In another embodiment, the user sets or inputs a value for low flow rate and/or high flow rate such as into the controller. In another embodiment, the low flow rate and/or high flow rate is not actually set. Rather, external data (such as data from the anatomical data sensor 1140) is used as the basis for affects the flow rate.

The flow control actuator 1165 can be multiple actuators, for example one actuator, such as a button or switch, to switch state from LO-FLOW to HI-FLOW and another to close the flow loop to OFF, for example during a contrast injection where the contrast is directed antegrade into the carotid artery. In an embodiment, the flow control actuator 1165 can include multiple actuators. For example, one actuator can be operated to switch flow rate from low to high, another actuator can be operated to temporarily stop flow, and a third actuator (such as a stopcock) can be operated for aspiration using a syringe. In another example, one actuator is operated to switch to LO-FLOW and another actuator is operated to switch to HI-FLOW. Or, the flow control actuator 1165 can include multiple actuators to switch states from LO-FLOW to HI-FLOW and additional actuators for fine-tuning flow rate within the high flow state and low flow state. Upon switching between LO-FLOW and HI-FLOW, these additional actuators can be used to fine-tune the flow rates within those states. Thus, it should be appreciated that within each state (i.e. high flow state and low flow states) a variety of flow rates can be dialed in and fine-tuned. A wide variety of actuators can be used to achieve control over the state of flow.

The controller 1130 or individual components of the controller 1130 can be located at various positions relative to the patient and/or relative to the other components of the system 100. For example, the flow control actuator 1165 can be located near the hemostasis valve where any interventional tools are introduced into the patient in order to facilitate access to the flow control actuator 1165 during introduction of the tools. The location may vary, for example, based on whether a transfemoral or a transcervical approach is used. The controller 1130 can have a wireless connection to the remainder of the system 100 and/or a wired connection of adjustable length to permit remote control of the system 100. The controller 1130 can have a wireless connection with the flow control regulator 125 and/or a wired connection of adjustable length to permit remote control of the flow control regulator 125. The controller 1130 can also be integrated in the flow control regulator 125. Where the controller 1130 is mechanically connected to the components of the flow control assembly 125, a tether with mechanical actuation capabilities can connect the controller 1130 to one or more of the components. In an embodiment, the controller 1130 can be positioned a sufficient distance from the system 100 to permit positioning the controller 1130 outside of a radiation field when fluoroscopy is in use.

The controller 1130 and any of its components can interact with other components of the system (such as the pump(s), sensor(s), shunt, etc) in various manners. For example, any of a variety of mechanical connections can be used to enable communication between the controller 1130 and the system components. Alternately, the controller 1130 can communicate electronically or magnetically with the system components. Electro-mechanical connections can also be used. The controller 1130 can be equipped with control software that enables the controller to implement control functions with the system components. The controller itself can be a mechanical, electrical or electro-mechanical device. The controller can be mechanically, pneumatically, or hydraulically actuated or electromechanically actuated (for example in the case of solenoid actuation of flow control state). The controller 1130 can include a computer, computer processor, and memory, as well as data storage capabilities.

Sensor(s)

As mentioned, the flow control assembly 125 can include or interact with one or more sensors, which communicate with the system 100 and/or communicate with the patient's anatomy. Each of the sensors can be adapted to respond to a physical stimulus (including, for example, heat, light, sound, pressure, magnetism, motion, etc.) and to transmit a resulting signal for measurement or display or for operating the controller 1130. In an embodiment, the flow sensor 1135 interacts with the shunt 120 to sense an aspect of the flow through the shunt 120, such as flow velocity or volumetric rate of blood flow. The flow sensor 1135 could be directly coupled to a display that directly displays the value of the volumetric flow rate or the flow velocity. Or the flow sensor 1135 could feed data to the controller 1130 for display of the volumetric flow rate or the flow velocity.

The type of flow sensor 1135 can vary. The flow sensor 1135 can be a mechanical device, such as a paddle wheel, flapper valve, rolling ball, or any mechanical component that responds to the flow through the shunt 120. Movement of the mechanical device in response to flow through the shunt 120 can serve as a visual indication of fluid flow and can also be calibrated to a scale as a visual indication of fluid flow rate. The mechanical device can be coupled to an electrical component. For example, a paddle wheel can be positioned in the shunt 120 such that fluid flow causes the paddle wheel to rotate, with greater rate of fluid flow causing a greater speed of rotation of the paddle wheel. The paddle wheel can be coupled magnetically to a Hall-effect sensor to detect the speed of rotation, which is indicative of the fluid flow rate through the shunt 120.

In an embodiment, the flow sensor 1135 is an ultrasonic or electromagnetic flow meter, which allows for blood flow measurement without contacting the blood through the wall of the shunt 120. An ultrasonic or electromagnetic flow meter can be configured such that it does not have to contact the internal lumen of the shunt 120. In an embodiment, the flow sensor 1135 at least partially includes a Doppler flow meter, such as a Transonic flow meter, that measures fluid flow through the shunt 120. It should be appreciated that any of a wide variety of sensor types can be used including an ultrasound flow meter and transducer. Moreover, the system can include multiple sensors.

The system 100 is not limited to using a flow sensor 1135 that is positioned in the shunt 120 or a sensor that interacts with the venous return device 115 or the arterial access device 110. For example, an anatomical data sensor 1140 can communicate with or otherwise interact with the patient's anatomy such as the patient's neurological anatomy. In this manner, the anatomical data sensor 1140 can sense a measurable anatomical aspect that is directly or indirectly related to the rate of retrograde flow from the carotid artery. For example, the anatomical data sensor 1140 can measure blood flow conditions in the brain, for example the flow velocity in the middle cerebral artery, and communicate such conditions to a display and/or to the controller 1130 for adjustment of the retrograde flow rate based on predetermined criteria. In an embodiment, the anatomical data sensor 1140 comprises a transcranial Doppler ultrasonography (TCD), which is an ultrasound test that uses reflected sound waves to evaluate blood as it flows through the brain. Use of TCD results in a TCD signal that can be communicated to the controller 1130 for controlling the retrograde flow rate to achieve or maintain a desired TCD profile. The anatomical data sensor 1140 can be based on any physiological measurement, including reverse flow rate, blood flow through the middle cerebral artery, TCD signals of embolic particles, or other neuromonitoring signals.

In an embodiment, the system 100 comprises a closed-loop control system. In the closed-loop control system, one or more of the sensors (such as the flow sensor 1135 or the anatomical data sensor 1140) senses or monitors a predetermined aspect of the system 100 or the anatomy (such as, for example, reverse flow rate and/or neuromonitoring signal). The sensor(s) feed relevant data to the controller 1130, which continuously adjusts an aspect of the system as necessary to maintain a desired retrograde flow rate. The sensors communicate feedback on how the system 100 is operating to the controller 1130 so that the controller 1130 can translate that data and actuate the components of the flow control regulator 125 to dynamically compensate for disturbances to the retrograde flow rate. For example, the controller 1130 may include software that causes the controller 1130 to signal the components of the flow control assembly 125 to adjust the flow rate such that the flow rate is maintained at a constant state despite differing blood pressures from the patient. In this embodiment, the system 100 need not rely on the user to determine when, how long, and/or what value to set the reverse flow rate in either a high or low state. Rather, software in the controller 1130 can govern such factors. In the closed loop system, the controller 1130 can control the components of the flow control assembly 125 to establish the level or state of retrograde flow (either analog level or discreet state such as high, low, baseline, medium, etc.) based on the retrograde flow rate sensed by the sensor 1135.

In an embodiment, the anatomical data sensor 1140 (which measures a physiologic measurement in the patient) communicates a signal to the controller 1130, which adjusts the flow rate based on the signal. For example the physiological measurement may be based on flow velocity through the MCA, TCD signal, or some other cerebral vascular signal. In the case of the TCD signal, TCD may be used to monitor cerebral flow changes and to detect microemboli. The controller 1130 may adjust the flow rate to maintain the TCD signal within a desired profile. For example, the TCD signal may indicate the presence of microemboli ("TCD hits") and the controller 1130 can adjust the retrograde flow rate to maintain the TCD hits below a threshold value of hits. (See, Ribo, et al., "Transcranial Doppler Monitoring of Transcervical Carotid Stenting with Flow Reversal Protection: A Novel Carotid Revascularization Technique", *Stroke* 2006, 37, 2846-2849; Shekel, et al., "Experience of 500 Cases of Neurophysiological Monitoring in Carotid Endarterectomy", *Acta Neurochir,* 2007, 149:681-689, which are incorporated by reference in their entirety.

In the case of the MCA flow, the controller 1130 can set the retrograde flow rate at the "maximum" flow rate that is tolerated by the patient, as assessed by perfusion to the brain. The controller 1130 can thus control the reverse flow rate to optimize the level of protection for the patient without relying on the user to intercede. In another embodiment, the feedback is based on a state of the devices in the system 100 or the interventional tools being used. For example, a sensor may notify the controller 1130 when the system 100 is in a high risk state, such as when an interventional catheter is positioned in the sheath 605. The controller 1130 then adjusts the flow rate to compensate for such a state.

The controller 1130 can be used to selectively augment the retrograde flow in a variety of manners. For example, it has been observed that greater reverse flow rates may cause a resultant greater drop in blood flow to the brain, most importantly the ipsilateral MCA, which may not be compensated enough with collateral flow from the Circle of Willis. Thus a higher reverse flow rate for an extended period of time may lead to conditions where the patient's brain is not getting enough blood flow, leading to patient intolerance as exhibited by neurologic symptoms. Studies show that MCA blood velocity less than 10 cm/sec is a threshold value below which patient is at risk for neurological blood deficit. There are other markers for monitoring adequate perfusion to the brains, such as EEG signals. However, a high flow rate may be tolerated even up to a complete stoppage of MCA flow for a short period, up to about 15 seconds to 1 minute.

Thus, the controller 1130 can optimize embolic debris capture by automatically increasing the reverse flow only during limited time periods which correspond to periods of heightened risk of emboli generation during a procedure. These periods of heightened risk include the period of time while an interventional device (such as the thrombectomy device 15) crosses the thrombotic occlusion 10. During lower risk periods, the controller can cause the reverse flow rate to revert to a lower, baseline level. This lower level may correspond to a low reverse flow rate in the ICA, or even slight antegrade flow in those patients with a high ECA to ICA perfusion pressure ratio.

In a flow regulation system where the user manually sets the state of flow, there is risk that the user may not pay attention to the state of retrograde flow (high or low) and accidentally keep the circuit on high flow. This may then lead to adverse patient reactions. In an embodiment, as a safety mechanism, the default flow rate is the low flow rate. This serves as a fail safe measure for patient's that are intolerant of a high flow rate. In this regard, the controller 1130 can be biased toward the default rate such that the controller causes the system to revert to the low flow rate after passage of a predetermined period of time of high flow rate. The bias toward low flow rate can be achieved via electronics or software, or it can be achieved using mechanical components, or a combination thereof. In an embodiment, the flow control actuator 1165 of the controller 1130 and/or valve(s) 1115 and/or pump(s) 1110 of the flow control regulator 125 are spring loaded toward a state that achieves a low flow rate. The controller 1130 is configured such that the user may over-ride the controller 1130 such as to manually cause the system to revert to a state of low flow rate if desired.

In another safety mechanism, the controller 1130 includes a timer 1170 (FIG. 15) that keeps time with respect to how long the flow rate has been at a high flow rate. The controller 1130 can be programmed to automatically cause the system 100 to revert to a low flow rate after a predetermined time period of high flow rate, for example after 15, 30, or 60 seconds or more of high flow rate. After the controller reverts to the low flow rate, the user can initiate another predetermined period of high flow rate as desired. Moreover, the user can override the controller 1130 to cause the system 100 to move to the low flow rate (or high flow rate) as desired.

In an exemplary procedure, embolic debris capture is optimized while not causing patient tolerance issues by initially setting the level of retrograde flow at a low rate, and then switching to a high rate for discreet periods of time during critical stages in the procedure. Alternately, the flow rate is initially set at a high rate, and then verifying patient tolerance to that level before proceeding with the rest of the procedure. If the patient shows signs of intolerance, the retrograde flow rate is lowered. Patient tolerance may be determined automatically by the controller based on feedback from the anatomical data sensor 1140 or it may be determined by a user based on patient observation. The adjustments to the retrograde flow rate may be performed automatically by the controller or manually by the user. Alternately, the user may monitor the flow velocity through the middle cerebral artery (MCA), for example using TCD, and then to set the maximum level of reverse flow which keeps the MCA flow velocity above the threshold level. In this situation, the entire procedure may be done without modifying the state of flow. Adjustments may be made as needed if the MCA flow velocity changes during the course of the procedure, or the patient exhibits neurologic symptoms.

Exemplary Mechanisms to Regulate Flow

The system 100 is adapted to regulate retrograde flow in a variety of manners. Any combination of the pump 1110, valve 1115, syringe 1120, and/or variable resistance component 1125 can be manually controlled by the user or automatically controlled via the controller 1130 to adjust the retrograde flow rate. Thus, the system 100 can regulate retrograde flow in various manners, including controlling an active flow component (e.g., pump, syringe, etc.), reducing the flow restriction, switching to an aspiration source (such as a pre-set VacLock syringe, Vacutainer, suction system, or the like), or any combination thereof.

In the situation where an external receptacle or reservoir is used, the retrograde flow may be augmented in various manners. The reservoir has a head height comprised of the height of the blood inside the reservoir and the height of the reservoir with respect to the patient. Reverse flow into the reservoir may be modulated by setting the reservoir height to increase or decrease the amount of pressure gradient from the CCA to the reservoir. In an embodiment, the reservoir is raised to increase the reservoir pressure to a pressure that is greater than venous pressure. Or, the reservoir can be positioned below the patient, such as down to a level of the floor, to lower the reservoir pressure to a pressure below venous or atmospheric pressure.

The variable flow resistance in shunt 120 may be provided in a wide variety of ways. In this regard, flow resistance component 1125 can cause a change in the size or shape of the shunt to vary flow conditions and thereby vary the flow rate. Or, the flow resistance component 1125 can re-route the blood flow through one or more alternate flow pathways in the shunt to vary the flow conditions. Some exemplary embodiments of the flow resistance component 1125 are now described.

As shown in FIGS. 16A, 16B, 16C, and 16D, in an embodiment the shunt 120 has an inflatable bladder 1205 formed along a portion of its interior lumen. As shown in FIGS. 16A and 16C, when the bladder 1205 is deflated, the inner lumen of the shunt 120 remains substantially unrestricted, providing for a low resistance flow. By inflating the bladder 1205, however, as shown in FIGS. 16B and 16D, the flow lumen can be greatly restricted, thus greatly increasing the flow resistance and reducing the flow rate of atrial blood to the venous vasculature. The controller 1130 can control inflation/deflation of the bladder 1205 or it can be controlled manually by the user.

Rather than using an inflatable internal bladder, as shown in FIGS. 16A-16D, the cross-sectional area of the lumen in the shunt 120 may be decreased by applying an external force, such as flattening the shunt 120 with a pair of opposed plates 1405, as shown in FIGS. 17A-17D. The opposed plates are adapted to move toward and away from one another with the shunt 120 positioned between the plates. When the plates 1405 are spaced apart, as shown in FIGS. 17A and 17C, the lumen of the shunt 120 remains unrestricted. When the plates 1405 are closed on the shunt 120, as shown in FIGS. 17B and 17D, in contrast, the plates 1405 constrict the shunt 120. In this manner, the lumen remaining in shunt 120 can be greatly decreased to increase flow resistance through the shunt. The controller 1130 can control movement of the plates 1405 or such movement can be controlled manually by the user.

Referring now to FIGS. 18A and 18B, the available cross-sectional area of the shunt 120 can also be restricted by axially elongating a portion 1505 of the shunt 120. Prior to axial elongation, the portion 1505 will be generally unchanged, providing a full luminal flow area in the portion 1505, as shown in FIG. 18A. By elongating the portion 1505, however, as shown in FIG. 18B, the internal luminal area of the shunt 120 in the portion 1505 can be significantly decreased and the length increased, both of which have the effect of increasing the flow resistance. When employing axial elongation to reduce the luminal area of shunt 120, it will be advantageous to employ a mesh or braid structure in the shunt at least in the portion 1505. The mesh or braid structure provides the shunt 120 with a pliable feature that facilitates axial elongation without breaking. The controller 1130 can control elongation of the shunt 120 or such it can be controlled manually by the user.

Referring now to FIGS. 19A-19D, instead of applying an external force to reduce the cross-sectional area of shunt 120, a portion of the shunt 120 can be made with a small diameter to begin with, as shown in FIGS. 19A and 19C. The shunt 120 passes through a chamber 1600 which is sealed at both ends. A vacuum is applied within the chamber 1600 exterior of the shunt 120 to cause a pressure gradient. The pressure gradient cause the shunt 120 to increase in size within the chamber 120, as shown in FIGS. 16B and 12D. The vacuum may be applied in a receptacle 1605 attached to a vacuum source 1610. Conversely, a similar system may be employed with a shunt 120 whose resting configuration is in the increased size. Pressure may be applied to the chamber to shrink or flatten the shunt to decrease the flow resistance. The controller 1130 can control the vacuum or it can be controlled manually by the user.

Figure 20A:
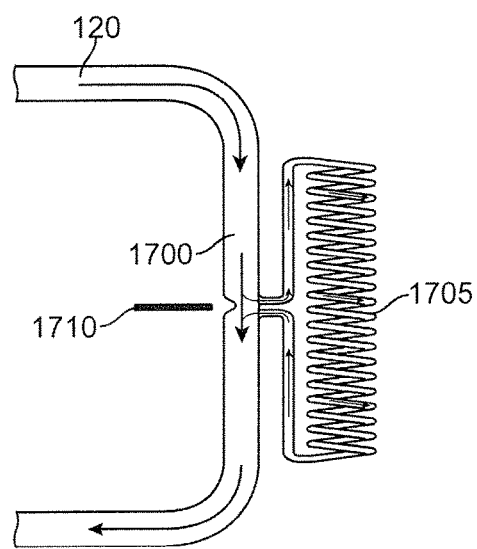
Figure 20B:
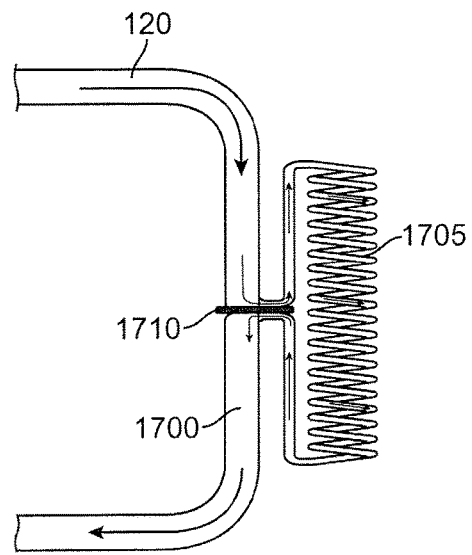

As yet another alternative, the flow resistance through shunt 120 may be changed by providing two or more alternative flow paths. As shown in FIG. 20A, the flow through shunt 120 passes through a main lumen 1700 as well as secondary lumen 1705. The secondary lumen 1705 is longer and/or has a smaller diameter than the main lumen 1700. Thus, the secondary lumen 1705 has higher flow resistance than the main lumen 1700. By passing the blood through both these lumens, the flow resistance will be at a minimum. Blood is able to flow through both lumens 1700 and 1705 due to the pressure drop created in the main lumen 1700 across the inlet and outlet of the secondary lumen 1705. This has the benefit of preventing stagnant blood. As shown in FIG. 20B, by blocking flow through the main lumen 1700 of shunt 120, the flow can be diverted entirely to the secondary lumen 1705, thus increasing the flow resistance and reducing the blood flow rate. It will be appreciated that additional flow lumens could also be provided in parallel to allow for a three, four, or more discrete flow resistances. The shunt 120 may be equipped with a valve 1710 that controls flow to the main lumen 1700 and the secondary lumen 1705 with the valve 1710 being controlled by the controller 1130 or being controlled manually by the user. The embodiment of FIGS. 20A and 20B has an advantage in that this embodiment in that it does not require as small of lumen sizes to achieve desired retrograde flow rates as some of the other embodiments of variable flow resistance mechanisms. This is a benefit in blood flow lines in that there is less chance of clogging and causing clots in larger lumen sizes than smaller lumen sizes.

Figure 21A:
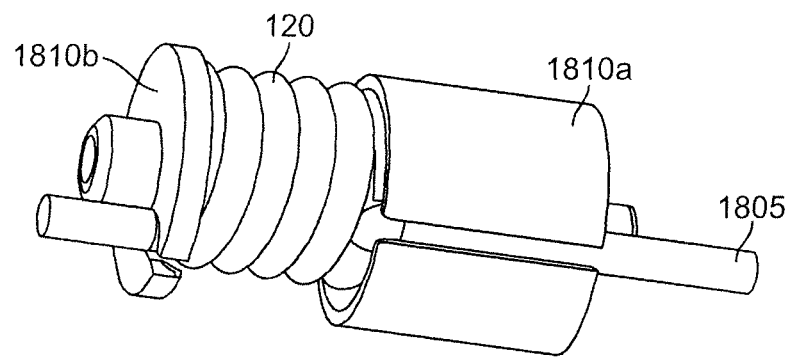
FIGS. 21A-21B, FIGS. 22A-22B, FIGS. 23A-23D, and FIGS. 24A-24B illustrate further embodiments of a variable flow resistance system useful in the methods and systems of the present disclosure.
Figure 21B:
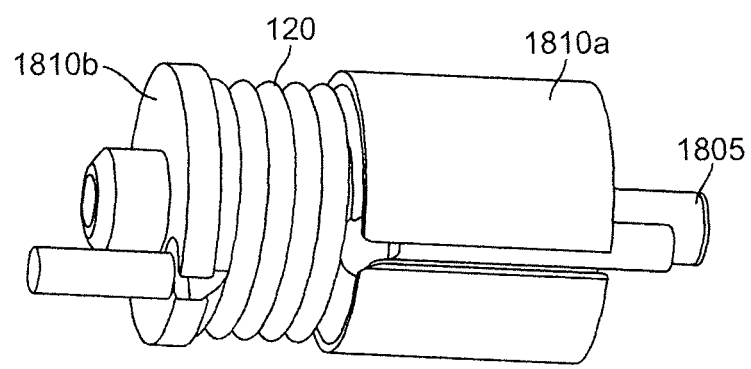

The shunt 120 can also be arranged in a variety of coiled configurations which permit external compression to vary the flow resistance in a variety of ways. Arrangement of a portion of the shunt 120 in a coil contains a long section of the shunt in a relatively small area. This allows compression of a long length of the shunt 120 over a small space. As shown in FIGS. 21A and 21B, a portion of the shunt 120 is wound around a dowel 1805 to form a coiled region. The dowel 1805 has plates 1810a and 1810b which can move toward and away from each other in an axial direction. When plates 1810a and 1810b are moved away from each other, the coiled portion of the shunt 105 is uncompressed and flow resistance is at a minimum. The shunt 120 is large diameter, so when the shunt is non-compressed, the flow resistance is low, allowing a high-flow state. To down-regulate the flow, the two plates 1810a and 1810b are pushed together, compressing the coil of shunt 120. By moving the plates 1810a and 1810b together, as shown in FIG. 21B, the coiled portion of the shunt 120 is compressed to increase the flow resistance. The controller 1130 can control the plates or they can be controlled manually by the user.

Figure 22A:
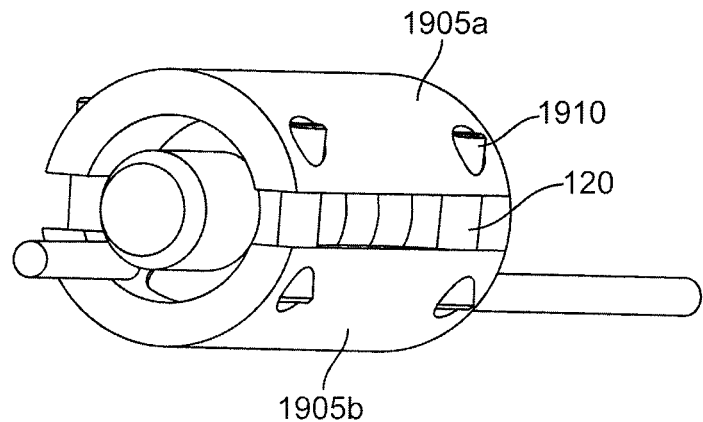
Figure 22B:
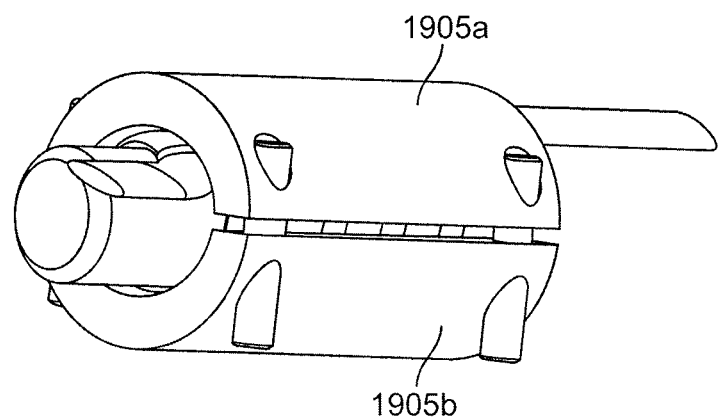

A similar compression apparatus is shown in FIGS. 22A and 22B. In this configuration, the coiled shunt 120 is encased between two movable cylinder halves 1905a and 1905b. The halves 1905a and 1905b can slide along dowel pins 1910 to move toward and away from one another. When the cylinder halves 1905 are moved apart, the coiled shunt 120 is uncompressed and flow resistance is at a minimum. When the cylinder halves 1905 are brought together, the coiled shunt 120 is compressed circumferentially to increase flow resistance. The controller 1130 can control the halves 1905 or they can be controlled manually by the user.

Figure 23A:
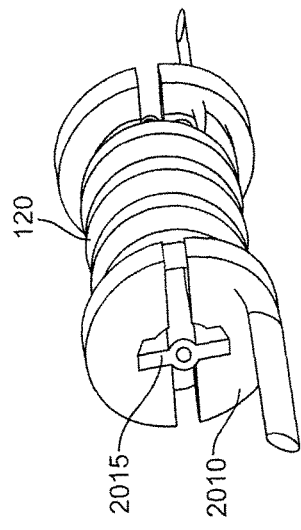
Figure 23D:
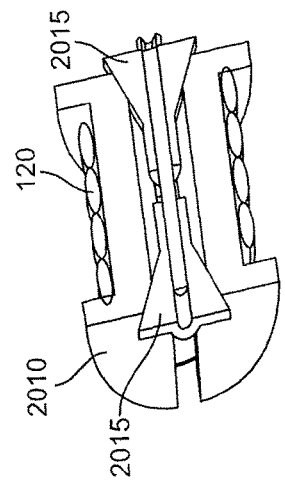
Figure 23B:
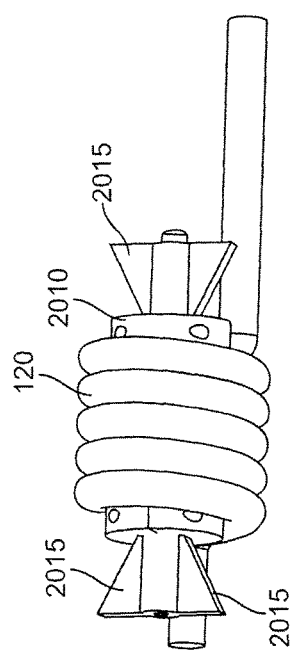
Figure 23C:
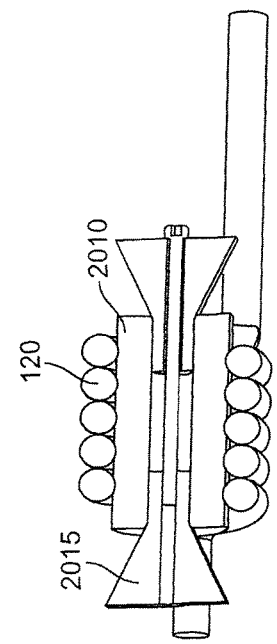

As shown in FIGS. 23A through 23D, the shunt 120 may also be wound around an axially split mandrel 2010 having wedge elements 2015 on opposed ends. By axially translating wedge elements 2015 in and out of the split mandrel 2010, the split portions of the mandrel are opened and closed relative to one another, causing the coil of tubing to be stretched (when the mandrel portions 2010 are spread apart, FIG. 23C, 23D) or relaxed (when the mandrel portions 2010 are closed, FIG. 23A, 23B.) Thus, when the wedge elements 2015 are spaced apart, as shown in FIGS. 23A and 23B, the outward pressure on the shunt 120 is at a minimum and the flow resistance is also at a minimum. By driving the wedge elements 2015 inwardly, as shown in FIGS. 23C and 23D, the split mandrel halves 2020 are forced apart and the coil of shunt 120 is stretched. This has the dual effect of decreasing the cross sectional area of the shunt and lengthening the shunt in the coiled region, both of which lead to increased flow resistance.

Figure 24A:
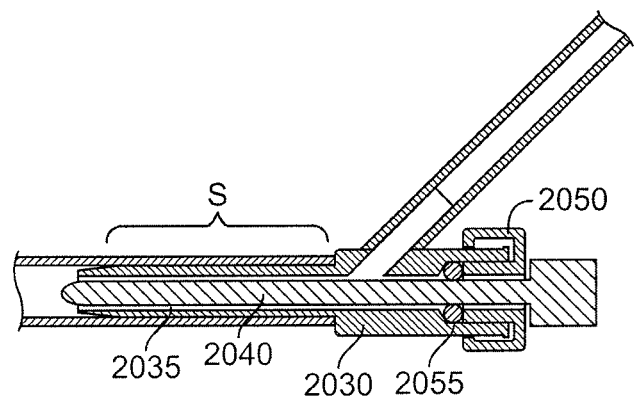
Figure 24B:
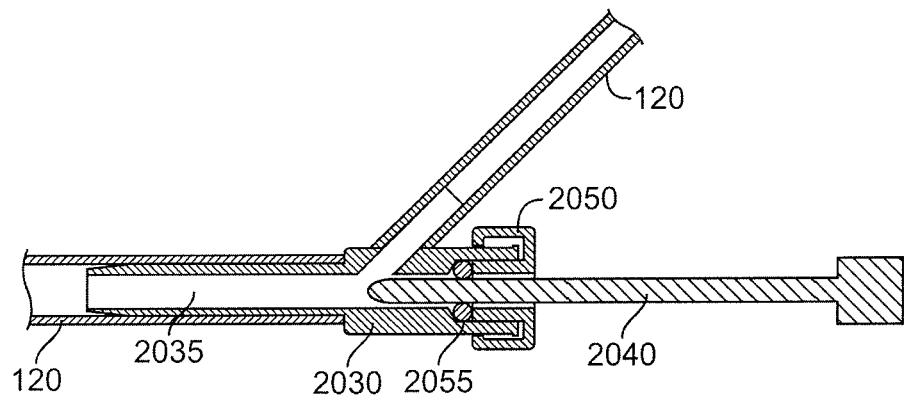

FIGS. 24A and 24B show an embodiment of the variable resistance component 1125 that uses a dowel to vary the resistance to flow. A housing 2030 is inserted into a section of the shunt 120. The housing 2030 has an internal lumen 2035 that is contiguous with the internal lumen of the shunt 120. A dowel 2040 can move into and out of a portion of the internal lumen 2035. As shown in FIG. 24A, when the dowel 2040 is inserted into the internal lumen 2035, the internal lumen 2035 is annular with a cross-sectional area that is much smaller than the cross-sectional area of the internal lumen 2035 when the dowel is not present. Thus, flow resistance increases when the dowel 2040 is positioned in the internal lumen 2035. The annular internal lumen 2035 has a length S that can be varied by varying the portion of the dowel 2040 that is inserted into the lumen 2035.

Thus, as more of the dowel 2040 is inserted, the length S of the annular lumen 2035 increases and vice-versa. This can be used to vary the level of flow resistance caused by the presence of the dowel 2040.

The dowel 2040 enters the internal lumen 2035 via a hemostasis valve in the housing 2030. A cap 2050 and an O-ring 2055 provide a sealing engagement that seals the housing 2030 and dowel 2040 against leakage. The cap 2050 may have a locking feature, such as threads, that can be used to lock the cap 2050 against the housing 2030 and to also fix the position of the dowel 2040 in the housing 2040. When the cap 2050 is locked or tightened, the cap 2050 exerts pressure against the O-ring 2055 to tighten it against the dowel 2040 in a sealed engagement. When the cap 2050 is unlocked or untightened, the dowel 2040 is free to move in and out of the housing 2030.

Any type of closing element, including a self-closing element, may be deployed about the penetration in the wall of the common carotid artery prior to withdrawing the sheath 605 at the end of the procedure. Usually, the closing element will be deployed at or near the beginning of the procedure, but optionally, the closing element could be deployed as the sheath is being withdrawn, often being released from a distal end of the sheath onto the wall of the artery where the penetration occurs, such as the common carotid artery. Use of a self-closing element is advantageous since it affects substantially the rapid closure of the penetration in the common carotid artery as the sheath is being withdrawn. Such rapid closure can reduce or eliminate unintended blood loss either at the end of the procedure or during accidental dislodgement of the sheath. In addition, such a self-closing element may reduce the risk of arterial wall dissection during access. Further, the self-closing element may be configured to exert a frictional or other retention force on the sheath during the procedure. Such a retention force is advantageous and can reduce the chance of accidentally dislodging the sheath during the procedure. A self-closing element eliminates the need for vascular surgical closure of the artery with suture after sheath removal, reducing the need for a large surgical field and greatly reducing the surgical skill required for the procedure.

The disclosed systems and methods may employ a wide variety of closing elements, typically being mechanical elements which include an anchor portion and a closing portion such as a self-closing portion. The anchor portion may comprise hooks, pins, staples, clips, tine, suture, or the like, which are engaged in the exterior surface of the common carotid artery about the penetration to immobilize the self-closing element when the penetration is fully open. The self-closing element may also include a spring-like or other self-closing portion which, upon removal of the sheath, will close the anchor portion in order to draw the tissue in the arterial wall together to provide closure. Usually, the closure will be sufficient so that no further measures need be taken to close or seal the penetration. Optionally, however, it may be desirable to provide for supplemental sealing of the self-closing element after the sheath is withdrawn. For example, the self-closing element and/or the tissue tract in the region of the element can be treated with hemostatic materials, such as bioabsorbable polymers, collagen plugs, glues, sealants, clotting factors, or other clot-promoting agents. Alternatively, the tissue or self-closing element could be sealed using other sealing protocols, such as electrocautery, suturing, clipping, stapling, or the like. In another method, the self-closing element will be a self-sealing membrane or gasket material which is attached to the outer wall of the vessel with clips, glue, bands, or other means. The self-sealing membrane may have an inner opening such as a slit or cross cut, which would be normally closed against blood pressure. Any of these self-closing elements could be designed to be placed in an open surgical procedure, or deployed percutaneously.

In an embodiment, the closing element is a is a suture-based blood vessel closure device that can perform the dilation of an arteriotomy puncture, and therefore does not require previous dilation of the arteriotomy puncture by a separate device or by a procedural sheath dilator. The suture-based vessel closure device can place one or more sutures across a vessel access site such that, when the suture ends are tied off after sheath removal, the stitch or stitches provide hemostasis to the access site. The sutures can be applied either prior to insertion of a procedural sheath through the arteriotomy or after removal of the sheath from the arteriotomy. The device can maintain temporary hemostasis of the arteriotomy after placement of sutures but before and during placement of a procedural sheath and can also maintain temporary hemostasis after withdrawal of the procedural sheath but before tying off the suture. Some exemplary suture-based blood vessel disclosure devices are described in the following U.S. Patents, which are incorporated herein by reference in their entirety: U.S. Pat. No. 7,001,400, and U.S. Pat. No. 7,004,952.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method for accessing an intracranial artery pursuant to a procedure to treat acute ischemic stroke, comprising:
    forming a penetration in a wall of a common carotid artery or internal carotid artery;
    applying a closure device at a very beginning of the procedure at a site of the penetration and before placement of any structure through the penetration including an arterial access sheath, the closure device having sutures;
    positioning an arterial access sheath having an occlusion element and an inner diameter that is between 7 Fr and 10 Fr through the penetration such that the occlusion element is positioned within the internal carotid artery;
    occluding the internal carotid artery;
    establishing retrograde blood flow through the internal carotid artery distal of the occluding element;
    inserting a distal catheter having an aspiration lumen into the intracranial artery through the access sheath, the distal catheter further having a distal-most end that defines an opening into the aspiration lumen
    treating a thrombotic blockage in the intracranial artery by positioning the distal-most end of the distal catheter so that the distal-most end is located immediately adjacent the thrombotic blockage in the intracranial artery;
    aspirating blood and/or material from the thrombotic blockage in the intracranial artery into the opening at the distal-most end of the distal catheter such that the aspiration causes the blood and/or material from the thrombotic blockage to flow into the opening at the distal-most end of the distal catheter;
    removing the arterial access sheath from the penetration; and
    closing the access site with the sutures of the closure device.

2. A method as in claim 1, wherein establishing retrograde blood flow through the internal carotid artery comprises causing blood to flow into a lumen of the arterial access sheath and into a shunt connected to the access sheath.

3. A method as in claim 2, further comprising regulating the retrograde blood flow.

4. A method as in claim 2, further comprising controlling a state of the retrograde blood flow.

5. A method as in claim 2, further comprising monitoring the retrograde blood flow.

6. A method as in claim 1, wherein treating a thrombotic blockage further comprises inserting a treatment device through the arterial access sheath and positioning at least a portion of the treatment device in the intracranial artery for the purpose of at least removing or disrupting the thrombotic blockage.

7. A method as in claim 6, wherein removing the thrombotic blockage further comprises aspirating the thrombotic blockage or debris generated from the thrombotic blockage.

8. A method as in claim 1, wherein treating a thrombotic blockage further comprises establishing a lumen through the thrombotic blockage.

9. A method as in claim 8, wherein establishing a lumen comprises implanting a temporary or permanent stent in the thrombotic blockage.

10. A method as in claim 1, wherein treating a thrombotic blockage further comprises infusing a bolus of thrombolytic drug through the arterial access sheath to the thrombotic blockage in the intracranial artery.

11. A method as in claim 1, wherein the occlusion element is a balloon.

* * * * *